United States Patent [19]

Urbach et al.

[11] Patent Number: 5,008,400
[45] Date of Patent: Apr. 16, 1991

[54] BICYCLIC AMINOACIDS AS INTERMEDIATES

[75] Inventors: Hansjörg Urbach, Kronberg; Rainer Henning, Frankfurt am Main; Volker Teetz, Hofheim am Taunus; Rolf Geiger, Frankfurt am Main; Reinhard Becker, Wiesbaden; Holger Gaul, Niederneisen, all of Fed. Rep. of Germany

[73] Assignee: Hoechst Aktiengesellschaft, Frankfurt, Fed. Rep. of Germany

[21] Appl. No.: 673,605

[22] Filed: Nov. 21, 1984

Related U.S. Application Data

[62] Division of Ser. No. 453,092, Dec. 27, 1982, abandoned.

[30] Foreign Application Priority Data

Dec. 29, 1981 [DE] Fed. Rep. of Germany ....... 3151690
Mar. 24, 1982 [DE] Fed. Rep. of Germany ....... 3210701

[51] Int. Cl.$^5$ .................. C07D 209/12; C07D 209/52
[52] U.S. Cl. .................................... 548/452; 546/158; 548/515
[58] Field of Search ........................................ 548/452

[56] References Cited

U.S. PATENT DOCUMENTS

| | | | |
|---|---|---|---|
| 4,344,449 | 11/1982 | Hoefle et al. | 546/147 |
| 4,350,704 | 9/1982 | Hoefle et al. | 514/412 |
| 4,404,206 | 9/1983 | Vincent et al. | 546/147 |
| 4,468,396 | 8/1984 | Magatti | 514/222 |
| 4,490,386 | 12/1984 | Seamans et al. | 514/419 |
| 4,559,340 | 12/1985 | Neustadt et al. | 514/222 |

FOREIGN PATENT DOCUMENTS

| | | |
|---|---|---|
| 75949/81 | 4/1982 | Australia . |
| 0037231 | 10/1981 | European Pat. Off. . |
| 46953 | 3/1982 | European Pat. Off. . |
| 0049605 | 4/1982 | European Pat. Off. . |
| 0049658 | 4/1982 | European Pat. Off. . |
| 50800 | 5/1982 | European Pat. Off. . |
| 0051301 | 5/1982 | European Pat. Off. . |
| 0031741 | 7/1981 | France . |
| T28389 | 12/1983 | Hungary . |
| T30000 | 2/1984 | Hungary . |

Primary Examiner—Glennon H. Hollrah
Assistant Examiner—James H. Turnipseed
Attorney, Agent, or Firm—Curtis, Morris & Safford

[57] ABSTRACT

Disclosed are cis, exo- and trans-compounds of the formula I

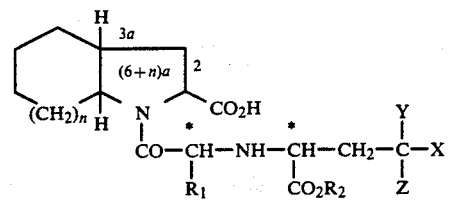

in which n denotes 0,1 or 2, $R_1$ denotes hydrogen, $(C_1-C_6)$-alkyl which can optionally by substituted by amino, $(C_1-C_4)$-acyl- or bezoylamino, $(C_2-C_6)$-alkenyl, $(C_5-C_9)$-cycloalkyl, $(C_5-C_9)$-cycloalkenyl, $(C_5-C_7)$-cycloalkyl-$(C_1-C_4)$-alkyl, aryl or partially hydrogenated aryl, which can, in each case, be substituted by $(C_1-C_2)$-alkyl, $(C_2-C_2)$-alkoxy or halogen, aryl-$(C_1-C_4)$-alkyl, /which can be substituted as defined previously in the aryl radical/, a monocyclic or bicyclic sulfur or nitrogen and/or nitrogen heterocyclic radical, or a side chain of naturally occurring aminoacid, $R_2$ denotes hydrogen, $(C_1-C_6)$-alkyl, $(C_2-C_6)$-alkenyl or aryl-$(C_1-C_4)$-alkyl, Y denotes hydrogen or hydroxyl, Z denotes hydrogen or Y and Z together denote oxygen, X denotes $(C_1-C_6)$-alkyl, $(C_2-C_6)$-alkenyl, $(C_5-C_9)$-cycloalkyl or aryl which can be mono-, di- or tri- substituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino or methylenedioxy, or indol-3-yl, or physiologically acceptable salts thereof, a process for the preparation thereof, agents containing them, their use as a medicine and intermediates for the preparation thereof.

5 Claims, No Drawings

BICYCLIC AMINOACIDS AS INTERMEDIATES

This application is a division of application Ser. No. 453,092, filed Dec. 27, 1982, now abandoned.

The present invention relates to new derivatives of the bicyclic aminoacids of the formula I

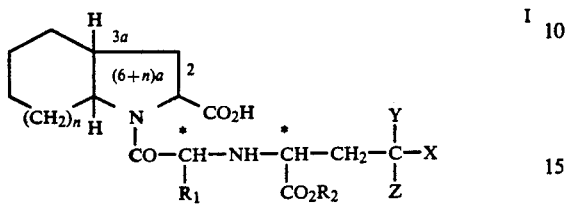

in which the hydrogen atoms on the bridgehead C atoms 3a and (6+n)a have the cis or trans configuration relative to one another, wherein, in the case of the cis configuration, the carboxyl group on C atom 2 is oriented exo to the bicyclic ring system and wherein n denotes 0, 1 or 2, $R_1$ denotes hydrogen, ($C_1$–$C_6$)-alkyl which can optionally be substituted by amino, ($C_1$–$C_4$)-acylamino or benzoylamino, ($C_2$–$C_6$)-alkenyl, ($C_5$–$C_9$)-cycloalkyl, ($C_5$–$C_9$)-cycloalkenyl, ($C_5$–$C_7$)-cycloalkyl-($C_1$–$C_4$)-alkyl, aryl or partially hydrogenated aryl, which can, in each case, be substituted by ($C_1$–$C_2$)-alkyl, ($C_1$–$C_2$)-alkoxy or halogen, aryl-($C_1$–$C_4$)-alkyl, [the aryl radical of which can be substituted as defined previously], a monocyclic or bicyclic heterocyclic radical having 5 to 7 or 8 to 10 ring atoms respectively, of which 1 to 2 ring atoms are sulfur or oxygen atoms and/or of which 1 to 4 ring atoms are nitrogen atoms, or a side chain of a naturally occurring aminoacid, $R_2$ denotes hydrogen, ($C_1$–$C_6$)-alkyl, ($C_2$–$C_6$)-alkenyl or aryl-($C_1$–$C_4$)-alkyl, Y denotes hydrogen or hydroxyl, Z denotes hydrogen or Y and Z together denote oxygen, X denotes ($C_1$–$C_6$)-alkyl, ($C_2$–$C_6$)-alkenyl, ($C_5$–$C_9$)-cycloalkyl or aryl which can be mono-, di- or tri-substituted by ($C_1$–$C_4$)-alkyl, ($C_1$–$C_4$)-alkoxy, hydroxyl, halogen, nitro, amino, ($C_1$–$C_4$)-alkylamino, di-($C_1$–$C_4$)-alkylamino or methylenedioxy, or indol-3-yl, and their physiologically acceptable salts.

Particularly suitable salts are alkali metal and alkaline earth metal salts, salts with physiologically tolerated amines and salts with inorganic or organic acids such as, for example, HCl, HBr, $H_2SO_4$, maleic acid and fumaric acid.

In this context and in the following text, aryl is to be understood as meaning phenyl or naphthyl. Alkyl can be straight-chain or branched.

In the case of the trans configuration of the H atoms on C-3a and C-(6+n)a, there are two possible configurations of the bicycle, and these are the $2\beta$, $3a\alpha$, $(6+n)a\beta$ configuration (part-formula Ib) and the $3\beta$, $3a\beta$, $(6+n)a\alpha$ configuration (part-formula Ic), whilst in the case of the cis configuration of the H atoms, the carboxyl group must be oriented in the exo-position (=$\beta$-position).

The exo-position (=$\beta$-position) of the carboxyl group on C-2 is defined so that the carboxyl group is oriented in the direction of the relevant H atoms, i.e. faces away from the concave side of the bicycle, for example corresponding to part-formula Ia. (For the definition of $\alpha$ and $\beta$, cf. Fieser and Fieser, Steroids, page 2, 1961).

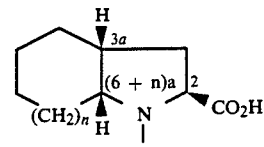

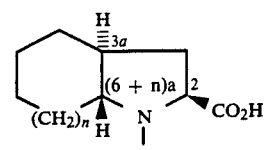

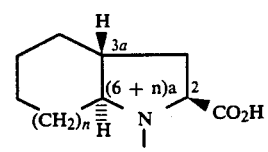

Compounds of the formula I have chiral C atoms in positions C-2, C-3a, C-(6+n)a, and in the C atoms labeled with an asterisk in the side chain. The invention relates to both the R and also the S configurations at all centers. The compounds of the formula I can thus be in the form of optical isomers, as diastereomers, as racemates or as mixtures thereof. Compounds of the formula I are preferred in which the C atom 2 in the bicyclic ring system and the C atoms labeled with an asterisk in the side chain have the S configuration.

Preferred compounds of the formula I are those in which $R_1$ denotes hydrogen, ($C_1$–$C_3$)-alkyl, ($C_2$–$C_3$)-alkenyl, benzyl or 4-aminobutyl, $R_2$ denotes hydrogen, ($C_1$–$C_4$)-alkyl or benzyl and X denotes phenyl which can be mono- or di-substituted or, in the case of methoxy, tri-substituted by ($C_1$–$C_2$)-alkyl, ($C_1$–$C_2$)-alkoxy, hydroxyl, fluorine, chlorine, bromine, amino, ($C_1$–$C_4$)-alkylamino, di-($C_1$–$C_4$)-alkylamino, nitro or methylenedioxy.

Compounds of the formula I are particularly preferred in which $R_1$ denotes methyl and X denotes phenyl and in which $R_2$ denotes hydrogen or ethyl.

Compounds of the formula I to which special attention is drawn are N-(1S-carboethoxy-3-phenyl-propyl)-S-alanyl-2S,3aR,6aR-octahydrocyclopenta[b]pyrrole-2-carboxylic acid, N-(1S-carboxy-3-phenyl-propyl)-S-alanyl-2S,3aR,7aR-octahydroindole-2-carboxylic acid, N-(1S-carboxy-3-phenyl-propyl)-S-alanyl-2S,3aR,6aR-octahydrocyclopenta[b]pyrrole-2-carboxylic acid, N-(1S-carboxy-3-phenyl-propyl)-S-alanyl-2S,3aR,7aS-octahydroindole-2-carboxylic acid and N-(1S-carboxy-3-phenyl-propyl)-S-alanyl-2S,3aS,7aR-octahydroindole-2-carboxylic acid, but especially N-(1S-carboethoxy-3-phenyl-propyl)-S-alanyl-2S,3aR,7aR-octahydroindole-2-carboxylic acid, N-(1S-carboethoxy-3-phenyl-propyl)-S-alanyl-2S,3aR,7aS-octahydroindole-2-carboxylic acid and N-(1S-carboethoxy-3-phenyl-propyl)-S-alanyl-2S,3aS,7aR-octahydroindole-2-carboxylic acid.

The invention further relates to processes for the preparation of the compounds of the formula I. One variant of the process comprises reacting, by methods for amide formation known in peptide chemistry, a compound of the formula II $$HO_2C-\underset{R_1}{\underset{|}{CH}}-NH-\underset{CO_2R_2}{\underset{|}{CH}}-CH_2-\underset{Z}{\overset{Y}{\underset{|}{\overset{|}{C}}}}-X \qquad \text{II}$$

wherein $R_1$, $R_2$, X, Y and Z have the meanings as in formula I, with a compound of the formula III (Formula III: bicyclic structure with $(CH_2)_n$, H atoms at 3a and (6+n)a positions, N-H, and $CO_2W$ group)

in which the H atoms on the C atoms 3a and (6+n)a have the cis or trans configuration relative to one another, wherein, in the case of the cis configuration, the group —$CO_2W$ is oriented exo to the bicyclic ring system and wherein n denotes 0, 1 or 2 and W denotes a radical which can be split off by hydrogenolysis or by acid, in particular a benzyl or a tert.-butyl radical, and then splitting off the radical W by catalytic hydrogenation or acid treatment and, where appropriate, also splitting off the radical $R_2$ by additional acid or base treatment, the free carboxylic acids being obtained in each case.

Further synthetic processes for the preparation of the compounds of the formula I, in which Y and Z together denote oxygen comprise reacting in a known manner in a Michael reaction (Organikum, 6th edition, page 492, 1967) a compound of the formula IV (Formula IV: bicyclic structure with $(CH_2)_n$, $CO_2W$, and $CO-CH(R_1)-NH_2$ substituent on N)

wherein the H atoms on the C atoms 3a and (6+n)a have the cis or trans configuration relative to one another, wherein in the case of the cis configuration, the group —$CO_2W$ is oriented exo to the bicyclic ring system, and wherein n and $R_1$ have the meanings as in formula I and W has the meaning as in formula III, with a compound of the formula V, $$R_2O_2C-CH=CH-CO-X \qquad \text{V}$$

wherein $R_2$ and X have the meanings as in formula I, and splitting off the radical W and, if appropriate, the radical $R_2$ as described above, or comprise reacting in a known manner in a Mannich reaction (Bull. Soc. Chim. France 1973, page 625) a compound of the abovementioned formula IV with a compound of the general formula VI, wherein $R_2$ has the meaning as in formula I, and with a compound of the general formula VII $$\text{OHC}-CO_2R_2 \qquad X-CO-CH_3$$
$$\text{VI} \qquad\qquad \text{VII}$$

wherein X has the meaning as in formula I, and subsequently splitting off the radical W and, if appropriate, the radical $R_2$ as described above to form the free carboxyl groups.

Furthermore, compounds of the formula I with Y and Z being hydrogen can also be prepared in such a manner that a compound of the abovementioned formula IV is reacted in accordance with the procedure described in J. Amer. Chem. Soc. 93 2897 (1971) with a compound of the formula VIII $$O=C\underset{CH_2-CH_2-X}{\overset{CO_2R_2}{\diagup}} \qquad \text{VIII}$$

wherein $R_2$ and X have the meanings as in formula I, and the Schiff's bases obtained are reduced and subsequently the radical W and, if appropriate, the radical $R_2$ are split off as described above to form the free carboxyl groups, or that a compound of the formula I, in which Y and Z together denote oxygen, obtained according to the above procedures is reduced catalytically with hydrogen. The reduction of the Schiff's bases can be carried out catalytically, electrolytically or with reducing agents, such as, for example, sodium borohydride or sodium cyanoborohydride.

Compounds of the formula I with Y being hydroxyl and Z being hydrogen can also be obtained, for example, by reduction of a compound I with Y and Z together being oxygen obtained according to the above procedure. This reduction can be carried out catalytically with hydrogen or with another reducing agent, such as, for example, sodium borohydride.

The invention further relates to compounds of the formula III'', in which n represents a whole number from 0 to 10, W' represents hydrogen, alkyl having 1 to 18 C atoms or aralkyl having 7 to 10 C atoms and $R_3$, $R_4$ and/or $R_5$ (Formula III'': bicyclic structure with $[CH_2]_n$, $R_4$, $R_5$, N-$R_3$, and COOW' group)

represent hydrogen, or $R_3$ and $R_4$ or $R_4$ and $R_5$ together each denote a chemical bond.

Preferred compounds of the formula III'' are compounds of the formula III'

(Formula III': bicyclic structure with $(CH_2)_n$, H atoms at 3a and (6+n)a positions, N-H, and $CO_2W'$ group)

wherein C-2, C-3a and C-(6+n)a have the same configuration as in formula III, n denotes 0, 1 or 2 and W' has the meaning of W in formula III and also denotes hydrogen. According to the invention, these compounds serve as starting materials for the synthesis of compounds of the formula I and can be prepared according to the invention by the following procedures.

One synthetic variant starts with a compound of the formula IX

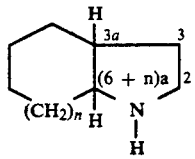

wherein the H atoms on the C atoms 3a and (6+n)a have the cis or trans configuration relative to one another and wherein n denotes the number 0, 1 or 2.

Compounds of the formula IX with n being 0 are known from Booth et al., J. Chem. Soc. 1959, page 1050, those with n being 1 are known from King et al., J. Chem. Soc. 1953, pages 250 and 253 and those with n being 2 are known from Ayerst et al., J. Chem. Soc. 1960, page 3445.

These compounds of the formula IX are acylated in a known manner, an aliphatic or aromatic acyl radical, preferably an acetyl or benzoyl radical, being bonded to the nitrogen atom, and the N-acylated compounds obtained are anodically oxidized (in analogy with Liebigs Ann. Chem. 1978 page 1719) in an aliphatic alcohol, preferably an alkanol having 1 to 4 C atoms, in particular methanol, in the presence of a conducting salt, preferably at temperatures in the range from 0° to +40° C. with formation of a compound of the formula X, wherein n denotes 0, 1 or 2 and

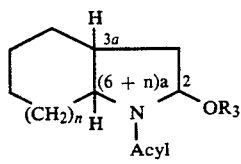

$R_3$ denotes $(C_1-C_4)$-alkyl.

The compound of the general formula X obtained is reacted with trimethylsilyl cyanide in accordance with Tetrahedron Letters 1981 page 141 in an aprotic organic solvent, such as, for example, in a hydrocarbon, halogenated hydrocarbon, in ether or in THF at temperatures in the range from −60° C. to +20° C., preferably −40° C. to ±0° C. in the presence of a Lewis acid, such as, for example, $ZnCl_2$, $SnCl_2$, $SnCl_4$, $TiCl_4$ or $BF_3$ etherate, preferably $BF_3$ etherate, and the compound of the formula XI obtained

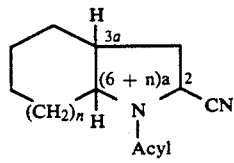

wherein the H atoms on the C atoms 3a and (6+n)a have the cis or trans configuration relative to one another, wherein in the case of the cis configuration, the group —CN is oriented exo to the bicyclic ring system and wherein n has the abovementioned meaning, after purification and separation from by-products by means of recrystallization or column chromatography, is hydrolyzed by the action of acid or bases in a known manner to give a compound of the formula III having W′=hydrogen, and the latter is esterified if appropriate. In particular, in the acid hydrolysis of the nitrile group, HCl or HBr is used as the acid. In this instance as in the following, the esterification is carried out by the procedures usual in amino-acid chemistry.

Compounds of the general formula III′ can also be prepared by converting, in a Beckmann rearrangement analogous to Helv. Chim. Acta 46, 1190 (1963), a compound of the formula XII

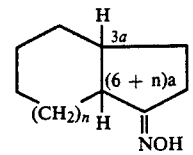

wherein the H atoms on the C atoms 3a and (6+n)a have the cis or trans configuration and n has the abovementioned meaning, into a compound of the formula XIII, wherein n has the abovementioned meaning,

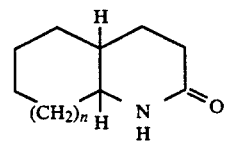

and the latter is halogenated to give a compound of the formula XIV

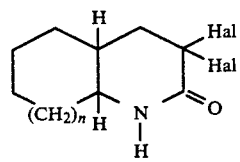

wherein n has the abovementioned meaning and Hal denotes a halogen atom, preferably chlorine or bromine. Examples of suitable halogenating agents are halides of inorganic acid, such as $PCl_5$, $SO_2Cl_2$, $POCl_3$, $SOCl_2$, $PBr_3$ or halogens, such as bromine. It is advantageous to use $PCl_5$ or $POCl_3$ combined with $SO_2Cl_2$. The intermediate initially formed is an imide halide, which, with the halogenating agent mentioned and subsequent hydrolysis under basic conditions, preferably with aqueous alkali metal carbonate, reacts further to give a compound of the formula XIV.

The compounds of the formula XIV are subsequently reduced catalytically in a polar protic solvent, such as, for example, an alcohol, preferably ethanol, or a carboxylic acid, such as, for example, acetic acid, with the addition of an acid acceptor, such as, for example, sodium acetate or triethylamine, to give a compound of the formula XV

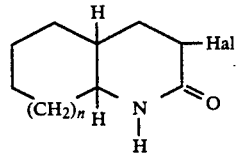

wherein n and Hal have the abovementioned meanings. Examples of suitable catalysts are Raney nickel or platinum on animal charcoal. Compounds of the formula XV can also be prepared directly by halogenation of the compounds of the formula XIII by using smaller amounts of the abovementioned halogenating agent.

Compounds of the formula XV are converted, in accordance with the known Favorskii reaction in the presence of a base, into a compound of the formula III' with W' being hydrogen, and the latter is esterified if appropriate. The abovementioned Favorskii reaction is carried out in an alcoholic solvent, such as methanol, ethanol or tert.-butanol, or in water or in mixtures thereof at temperatures in the range from 20° to 140° C., preferably between 60° and 100° C. Bases which are advantageously employed are alkali metal or alkaline earth metal hydroxides, such as sodium, potassium or barium hydroxide or alkali metal alcoholates, such as, for example, sodium methylate or potassium tert.-butanolate.

Furthermore, the compounds of the formula III', wherein the H atoms on the C atoms 3a and (6+n)a have the cis configuration, can be prepared from the compound of the formula XVI, wherein n denotes 0, 1 or 2,

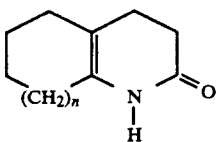

XVI by reducing the latter by means of platinum oxide/acetic acid in accordance with Ann. Chim. 62, 200 (1972) to give a compound of the abovementioned formula XIII and reacting the latter in accordance with the procedures described above. Compounds of the formula XVI are known from J. Org. Chem. 29, 2780 (1964).

Compounds of the formula III', in which the H atoms on the C atoms 3a and (6+n)a have the trans configuration, can also be prepared from a compound of the abovementioned formula XVI by reducing the latter with sodium formate/formic acid in accordance with Bull. Soc. Chim. Belg. 85 11 (1976) to give a compound of the formula XIII and reacting the latter further in accordance with the procedures described above.

Trans-configurated 2-azabicycloalkane-3-carboxylic acids of the formula III', in which n denotes a whole number from 0 to 10 and W' represents hydrogen, and their alkyl and aralkyl esters can be prepared from enamines of the formula XVII in which n has the previous meaning and $X^1$ represents dialkylamino having 2 to 10 C atoms or a radical of the formula XVIIa, wherein m and o denote a whole number from 1 to 3, $(m+o) \geq 3$ and A denotes $CH_2$, NH, O or S (Organikum, 6th edition, page 370, 1967),

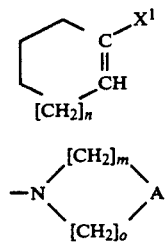

XVII

XVIIa together with N-acylated β-halogeno-α-aminopropionates of the formula XVIII (for the free amino compound, cf. Helv. Chim. Acta 40, 1541 (1957)), in which $X^2$ represents halogen, preferably chlorine or bromine, $Y^1$ represents alkanoyl having 1 to 5 C atoms, aroyl having 7 to 9 C atoms or other protective groups which are customary in peptide chemistry and which can be split off by acid, and $R_4'$ represents alkyl having 1 to 5 C atoms or aralkyl having 7 to 9 C atoms,

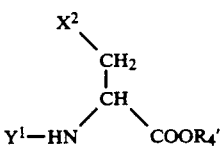

XVIII or together with acrylates of the formula XIX (Chem. Ber. 91 2427 (1958)), in which $Y^1$ and $R_4'$ have the previous meaning

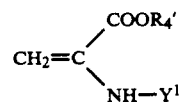

XIX to give compounds of the formula XX, in which $R_4'$ and $Y^1$ have the previous meaning,

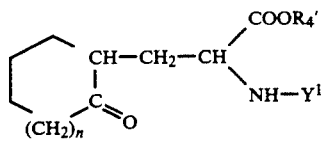

XX the latter are cyclized, with acylamide and ester cleavage, by means of strong acids to give compounds of the formula XXIa, which can also be in the tautomeric form of the formula XXIb, and in which n has the previous meaning

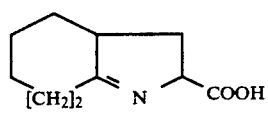

XXIa

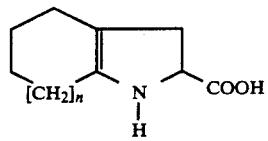

XXIb and the compounds of the formula XXIa or b, if appropriate after conversion into their $C_1$-$C_{18}$-alkyl or $C_7$-$C_{10}$-aralkyl esters, are converted by catalytic hydrogenation in the presence of transition metal catalysts or by reduction with borane-amine complexes or complex borohydrides, into trans-configurated compounds of the formula III', in which n has the previous meaning and W' represents hydrogen, alkyl having 1 to 18 C atoms or aralkyl having 7 to 10 C atoms, and esters of the formula III' are saponified if appropriate, and the latter, if W' is hydrogen, esterified, if appropriate, to give compounds of the formula III' in which n has the previous meaning and W' represents alkyl having 1 to 18 C atoms or aralkyl having 7 to 10 C atoms.

The reaction of 3-bromopropylamine with an enamine of cyclohexanone is described in Am. Soc. 81 (1956) 2596. It is also stated that a free $NH_2$ group is necessary for successful alkylation. Thus it is extremely surprising that even halogenopropionic acid derivatives having an acylated amino group, as do the compounds of the formula XVIII described previously, can be employed for the alkylation of enamines. Enamines of cyclohexanone or cycloheptanone are preferably employed for this purpose. Examples of suitable amine components are diethylamine, pyrrolidine, piperidine or morpholine. However, other secondary amines are also suitable. Pyrrolidinocycloalkylenes are preferred.

Particularly suitable groups $Y^1$ in the β-bromo- or chloro-α-aminocarboxylates of the formula XVIII are formyl, acetyl, propionyl or benzoyl, or other protective groups which can be split off with acid, such as, for example, tert.-butyloxycarbonyl. The $C_1$-$C_3$-alkyl or the benzyl esters are preferably employed.

The acrylic acid derivatives of the formula XIX, which are produced as intermediates from the β-halogeno-α-aminopropionates under the basic conditions of the experiment, are also suitable as the starting compounds. They are prepared, for example, by treatment of the halogenoaminopropionic acid derivatives or the analogous o-tosylserine derivatives with bases. Tertiary organic bases, such as, for example, triethylamin are preferably used. It is advantageous to carry out the reaction with the addition of small amounts of polymerization inhibitors, such as, for example, hydroquinone in organic solvents. The acrylic acid derivatives of the formula XIX can be employed instead of the halogenopropionic acid derivatives under identical reactions conditions.

Suitable solvents for the enamine synthesis are organic solvents which cannot be alkylated, such as, for example, dimethylacetamide, DMSO, THF or toluene. Dimethylformamide is particularly suitable.

It is advisable to employ the enamines of the formula XVII in excess in order to avoid impurities of N-acylacrylates in the final product.

The hydrolysis of the N-acyl group necessary for cyclization is generally brought about at the same time as cleavage of the ester function by strong aqueous mineral acids, such as sulfuric acid or, preferably, hydrochloric acid. In the case of the N-tert.-butyloxycarbonyl derivatives of the formula XVII, it is possible, for example, on using dioxane/HCl or anhydrous trifluoroacetic acid, to retain the ester functionality and to isolate the esters of the dehydrocarboxylic acids XXIa or XXIb. The latter can be converted by hydrogenation in the presence of metal catalysts or reaction with borane-amine complexes or complex borohydrides into the trans-configurated 2-azabicyclocarboxylates of the formula III'.

Noble metal or nickel catalysts are suitable for catalytic hydrogenation. The isomeric ratio occurring on catalytic hydrogenation depends on the reaction conditions and the type of catalyst used.

It is possible to shorten the reaction time by increasing the pressure of hydrogen, but the temperature should be kept low. Examples of suitable solvents for the catalytic hydrogenation are ethanol, methanol, ethyl acetate, dioxane, glacial acetic acid or mixtures of these solvents.

Compounds of the formula III'b, in which n represents a whole number from 0 to 10 and W' represents hydrogen,

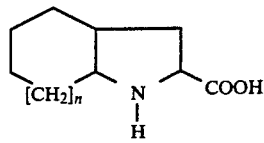

III'b can, also be obtained by reduction of compounds of the formulae XXIa or b, in which n has the previous meaning, with borane-amine complexes or complex borohydrides in lower alcohols. The preferred reducing agent is sodium borohydride in alcohols, in particular in methanol, ethanol or isopropanol. Amine-borane complexes in glacial acetic acid can equally be used.

Isolation of the pure trans compounds of the formula III'b can, for example, be carried out by chromatographic processes or crystallization processes.

The pure trans compound of the formula III'b is advantageously separated out of the mixture of diastereomers from the amine-borane-complex or boronate reduction by fractional crystallization.

The compounds of the formula III' can, if appropriate, be converted into the $C_1$-$C_{18}$-alkyl or $C_7$-$C_{10}$-aralkyl esters by methods which are described, for example, in Houben-Weyl, volume VIII (1952).

The compounds of the formula II with Y and Z being hydrogen, $R_1$ being methyl and $R_2$ being methyl or ethyl and X being phenyl which are used as starting materials for the preparation of the compounds of the formula I are known (European Patent Application No. 37,231). The compounds of the formula II can be prepared by various procedures. One sythetic variant starts from a ketone of the abovementioned formula VII, which is reacted by known procedures in a Mannich reaction with a compound of the abovementioned formula VI together with aminoacid esters of the formula XXII

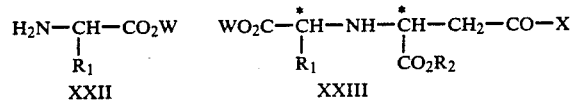

wherein $R_1$ and W have the abovementioned meanings, to give a compound of the formula XXIII, wherein $R_1$, $R_2$, X and W have the abovementioned meanings, with the proviso that in the case where W denotes a radical which can be split off by hydrogenolysis, in particular benzyl, $R_2$ may not have the meaning of W. If the radical W is split off by hydrogenolysis using, for example, palladium, compounds of the formula II with Y and Z being hydrogen are obtained. If the radical W is split off with acids, such as, for example, trifluoroacetic acid or hydrochloric acid in an inert organic solvent, such as, for example, dioxane, compounds of the formula II with Y and Z together being oxygen are obtained.

Compounds of the formula XXIII can also be obtained by Michael addition of a compound of the abovementioned formula V with a compound of the abovementioned formula XXII by known procedures. Preferentially, this process is suitable for the preparation of those compounds of the formula XXIII in which $R_1$ denotes methyl, $R_2$ denotes ethyl and X denotes aryl.

The compounds of the formula XXIII are obtained as mixtures of diastereomers. Preferred diastereomers of the formula XXIII are those in which the chiral C atoms labeled with an asterisk are each in the S configuration. These can be separated out by recrystallization or by chromatography, for example on silica gel. The configurations of the chiral C atoms are maintained during the subsequent splitting off of the radical W.

The compounds of the abovementioned formula IV used as starting materials for the preparation of the compounds of the formula I are obtained by known procedures from compounds of the abovementioned formula III by reaction with an N-protected 2-aminocarboxylic acid of the formula XXIV $$V-HN-\underset{R_1}{CH}-CO_2H \qquad XXIV$$

wherein V is a protective group and $R_1$ has the abovementioned meaning. Examples of suitable protective groups V, which are split off again after completion of the reaction, are the groups benzyloxycarbonyl or tert.-butoxycarbonyl.

The reaction of a compound of the formula II with a compound of the formula III to prepare a compound of the formula I is carried out by a condensation reaction known in peptide chemistry, the condensing agent added being, for example, dicyclohexylcarbodiimide and 1-hydroxybenzotriazole. In the subsequent removal of the radical W by hydrogenolysis, the catalyst used is preferably palladium, while the acids employed for the acid removal of the radical W are preferably trifluoroacetic acid or hydrogen chloride.

In the reactions described above for the preparation of the compounds of the formulae III', IV and I, the configurations at the bridgehead C atoms 3a and (6+n)a in the intermediate products are retained in each case. In the case of the trans configuration of the H atoms on the C atoms 3a and (6+n)a, the relevant compounds are obtained, in some cases, as pure diastereomers, and in other cases, as mixtures of diastereomers, which have the 2β, 3aα, (6+n)aβ or the 2β, 3aβ, (6+n)aα configuration as indicated above. These isomers can easily be separated by recrystallization or chromatography. If, for the preparation of the compounds of the formulae III', IV or I, corresponding starting materials having the cis configuration of the H atoms on C-3a and C-(6+n)a are employed, the exo (or β) isomers are obtained almost exclusively, and small proportions of the other isomers can be removed by recrystallization or by chromatography.

The compounds of the formula III' obtained according to the procedures described above are produced as racemic mixtures and can be employed as such in the further syntheses described above. However, they can also be employed as the pure enantiomers after separation of the racemates into the optical antipodes by customary methods, for example, via salt formation with optically active bases or acids.

If the compounds of the formula I are produced as racemates, these can also be resolved into their enantiomers by customary methods, such as, for example, via salt formation with optically active bases or acids.

The compounds of the formula I according to the invention are in the form of internal salts. Since they are amphoteric compounds, they can form salts with acids or bases. These salts are prepared in a customary manner by reaction with one equivalent of acid or base.

The compounds of the formula I and their salts have long-lasting and powerful hypotensive activities. They are strong inhibitors of the angiotensin converting enzyme (ACE inhibitors). They can be employed to control high blood pressure of various etiologies. It is also possible to combine them with other compounds having hypotensive, vasodilator or diuretic activity. Typical representatives of these classes of active compounds are described, for example, in Erhardt-Ruschig, Arzneimittel (Drugs), 2nd edition, Weinheim, 1972. They can be used intravenously, subcutaneously or perorally.

The dosage on oral administration is 1–100 mg, preferably 1–40 mg, for a single dose for an adult patient of normal weight. This can also be increased in severe cases, since no toxic properties have been observed hitherto. A decrease in the dose is also possible and is particularly appropriate when diuretics are administered concurrently.

The compounds according to the invention can be administered orally or parenterally in an appropriate pharmaceutical formulation. For a form for oral use, the active compounds are mixed with the additives customary for this purpose, such as vehicles, stabilizers or inert diluents and converted by customary methods into suitable forms for administration, such as tablets, coated tablets, hard capsules, aqueous, alcoholic or oily suspensions or aqueous, alcoholic or oily solutions. Inert vehicles which can be used are, for example, gum arabic, magnesium carbonate, potassium phosphate, lactose, glucose or starch, particularly corn starch. In this context, the formulation can either be as dry or as moist granules. Examples of suitable oily vehicles or solvents are plant and animal oils, such as sunflower oil or cod-liver oil.

For subcutaneous or intravenous administration, the active compounds or their physiologically tolerated salts are converted into solutions, suspensions or emulsions, if desired together with the substances customary for this purpose such as solubilizers, emulsifiers or other auxiliaries. Examples of suitable solvents for the new active compounds and the corresponding physiologically tolerated salts are: water, physiological saline or alcohols, for example ethanol, propanediol or glycerol, additionally also sugar solutions, such as glucose or mannitol solutions, or also a mixture of the various solvents mentioned.

The extremely high activity of the compounds according to formula I is demonstrated by the pharmacological data in the following tables: Intraduodenal administration to the anesthetized rat, 50% inhibition of the pressor reaction induced by 310 ng of angiotensin I 30 min. after administration in the dose . . . =$ED_{50}$:

TABLE I

| (H atoms on C-3a and C-(6 + n)a in formula I have the cis configuration) | | | | | | |
|---|---|---|---|---|---|---|
| n | X | Y | Z | $R_2$ | $R_1$ | $ED_{50}$ (μg/kg) |
| 0 | 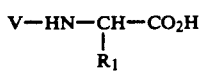 | H | H | $C_2H_5$ | $CH_3$ | 40 |
| 0 | 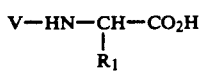 | H | H | H | $CH_3$ | 700 |

TABLE I-continued (H atoms on C-3a and C-(6 + n)a in formula I have the cis configuration)

| n | X | Y | Z | $R_2$ | $R_1$ | $ED_{50}$ (μg/kg) |
|---|---|---|---|---|---|---|
| 1 | phenyl | H | H | $C_2H_5$ | $CH_3$ | 50 |
| 1 | phenyl | H | H | H | $CH_3$ | 600 |
| 2 | phenyl | H | H | $C_2H_5$ | $CH_3$ | 230 |
| 2 | phenyl | H | H | H | $CH_3$ | 840 |
| 1 | phenyl | | O | $C_2H_5$ | $CH_3$ | 390 |

The symbols n, X, Y, Z, $R_1$ and $R_2$ relate to the compound of the formula I.

TABLE II

H atoms on C-3a and C-(6 + n)a have the trans configuration; X = phenyl, $R_1$ = methyl

| n | Y | Z | $R_2$ | Configuration of the bicycle | $ED_{50}$ (μg/kg) |
|---|---|---|---|---|---|
| 0 | H | H | H | 2S, 3aR, 6aS | 700 |
| 0 | H | H | $C_2H_5$ | 2S, 3aR, 6aS | 40 |
| 1 | H | H | H | 2S, 3aR, 7aS | 800 |
| 1 | H | H | $C_2H_5$ | 2S, 3aR, 7aS | 55 |
| 1 | H | H | H | 2S, 3aS, 7aR | 850 |
| 1 | H | H | $C_2H_5$ | 2S, 3aS, 7aR | 65 |
| 2 | H | H | H | 2S, 3aR, 8aS | 1080 |
| 2 | H | H | $C_2H_5$ | 2S, 3aR, 8aS | 110 |
| 1 | | O | $C_2H_5$ | 2S, 3aR, 7aS | 180 |

The symbols m, X, Y, Z, $R_1$ and $R_2$ relate to the compounds of the formula I.

The following examples serve to illustrate the invention but do not restrict it to the compounds mentioned as representatives:

EXAMPLE 1

2β,3aβ,7aβ-Octahydroindole-2-carboxylic acid (a) N-Acetyl-3aβ,7aβ-octahydroindole 3.5 g of platinum oxide were added to a solution of 77 g of indole in 700 ml of glacial acetic acid. The compound was initially hydrogenated under 100 atmospheres at 20° to 25° C. for 16 hours and then at 20° to 25° C. under normal pressure until the uptake of hydrogen was complete. The catalyst was filtered off with suction and the solvent was distilled off in vacuo. The residue was taken up in water and made alkaline with saturated potassium carbonate solution. After saturation with sodium chloride, the aqueous phase was extracted four times with methylene chloride and the organic phase was dried and evaporated.

The residue was taken up in 250 ml of pyridine, 93 ml of acetic anhydride were added and the mixture was allowed to react at 20° to 25° C. for 12 hours. After distilling off the pyridine, water was added to the residue and the mixture was made alkaline with concentrated aqueous sodium hydroxide. The aqueous phase was extracted with methylene chloride, the organic phase obtained was washed with 2N hydrochloric acid and with water. After drying and concentrating the solution, the residue was distilled.

Yield: 85 g; b.p.: 91° to 95° C./0.2 mm Hg.

(b) N-Acetyl-2-methoxy-3aβ,7aβ-octahydroindole 54 g of N-acetyl-3aβ,7aβ-octahydroindole were anodically oxidized in methanol, with the addition of tetramethylammonium tetrafluoborate, according to the details in Liebigs Ann. Chem. 1978, page 1790. The solvent was distilled off and the residue was filtered through 500 g of silica gel by means of ethyl acetate. 53.6 g of the abovementioned product were obtained from the ethyl acetate solution after evaporation. $R_f$ value (thin-layer chromatogram): 0.33 (silica gel, ethyl acetate).

(c) N-Acetyl-2β,3aβ,7aβ-octahydroindole-2-carbonitrile 25 g of trimethylsilyl cyanide in 50 ml of methylene chloride were added dropwise to a solution of 49.8 g of N-acetyl-2-methoxy-3aβ,7aβ-octahydroindole in 250 ml of methylene chloride at −40° C. Subsequently, 35.9 g of boron trifluoride etherate were added dropwise so that the temperature of the reaction mixture did not exceed −20° C. After 2 hours of reaction at −20° C., the temperature was slowly raised to 0° C., the mixture was stirred overnight at 0° C. and then for one hour at 20° to 25° C. Water was added to the mixture and this was stirred 10 min. The aqueous phase was extracted three times with methylene chloride. The combined organic extracts were dried, concentrated and the residue was triturated with diisopropyl ether.

Yield: 47 g; m.p. 128° to 130° C.

(d) 2β,3aβ,7aβ-Octahydroindole-2-carboxylic acid 10 g of N-acetyl-2β,3aβ,7aβ-octahydroindole-2-carbonitrile in 30 ml of concentrated hydrogen bromide were heated to boiling for 2 hours. After distilling off the hydrogen bromide, the residue was stirred with a little acetone and filtered off with suction.

An aqueous solution of the product was adjusted to a pH of 6.0 with a weakly basic ion exchanger. After filtration, the solution was evaporated and the residue was filtered through silica gel with a mixture of methylene chloride, methanol, glacial acetic acid and water in the ratio 20:10:0.5:0.5. The eluate was concentrated and the residue was triturated with diisopropyl ether.

Yield: 7.6 g.

$^1$H NMR spectrum*: 1.0–2.5 (m, 11H); 3.4–3.9 (m, 1H); 4.0–4.5 (m, 1H); 7.5–8.3 (broad s, exchangeable with $D_2O$).

*Here and in the following text, the $^1$H NMR data were obtained in $CDCl_3$ and are reported in ppm.

When the process was carried out in analogy to the procedures described under Example 1, the compounds mentioned under Example 2 and Example 3 in the following text were obtained:

EXAMPLE 2

2β,3aβ,6aβ-Octahydrocyclopenta[b]pyrrole-2-carboxylic acid (a) N-Acetyl-cis-octahydrocyclopenta[b]pyrrole $^1$H NMR data: 1.0 to 2.3 (m 9H); 2.0 (d, 3H); 3.3 to 4.2 (m, 3H).

(b) Acetyl-2-methoxy-cis-octahydrocyclopenta[b]pyrrole $^1$H NMR data: 0.9 to 2.6 (m, 9H); 2.1 (s, 3H); 3.3 (s, 3H); 3.8–4.3 (m, 1H); 4.7–5.5 (m, 1H).

(c) N-Acetyl-2-cyano-cis-octahydrocyclopenta[b]pyrrole $^1$H-NMR data: 1.0–3.0 (m, 9H); 2.1 (d, 3H); 3.5–4.1 (m, 1H); 4.4–4.7 (m, 1H).

(d) 2β,3aβ,6aβ-Octahydrocyclopenta[b]pyrrole-2-carboxylic acid $^1$H NMR data: 1.0–2.3 (m, 9H); 3.5–3.9 (m, 1H); 4.0–4.6 (m, 1H); 7.7–8.4 (broad s, exchangeable with D$_2$O).

EXAMPLE 3

2β,3aβ,8aβ-Decahydrocyclohepta[b]pyrrole-2-carboxylic acid (a) N-Acetyl-cis-decahydrocyclohepta[b]pyrrole $^1$H NMR data: 0.9–2.5 (m, 13H); 2.1 (s, 3H); 3.1–4.1 (m, 3H).

(b) N-Acetyl-2-methoxy-cis-decahydrocyclohepta[b]pyrrole $^1$H NMR data: 0.9–2.7 (m, 13H); 2.1 (s, 3H); 3.2 (s, 3H); 3.7–4.2 (m, 1H); 4.7–5.3 (m, 1H).

(c) N-Acetyl-2-cyano-cis-decahydrocyclohepta[b]pyrrole $^1$H NMR data: 0.9–3.1 (m, 13H); 2.1 (s, 3H); 3.5–4.1 (m, 1H); 4.3–4.7 (m, 1H).

(d) 2β,3aβ,8aβ-Decahydrocyclohepta[b]pyrrole-2-carboxylic acid $^1$H NMR data: 0.8–2.4 (m, 13H); 3.5–3.9 (m, 1H); 4.1–4.6 (m, 1H); 7.6–8.3 (broad s, exchangeable with D$_2$O).

EXAMPLE 4

2β,3aβ,7aβ-Octahydroindole-2-carboxylic acid (a) 3,4,5,6,7,8-Hexahydro-1H-quinolin-2-one 392 g of cyclohexanone and 212 g of acrylonitrile together with 20 g of cyclohexylamine, 4 g of glacial acetic acid and 0.4 g of hydroquinone were heated under reflux for 4 hours up to a final temperature of 200° C. After distillation at 100° to 150° C./0.5 mm Hg, the residue remaining, which contained the desired product, was recrystallized from n-hexane.

The distillate was heated with 10 ml of 10% strength acetic acid at 200° C. for 2 days. After cooling down, further product was obtained which was crystallized from methanol/water.

A total of 460 g of title compound was obtained, m.p.: 143°–144° C.

(b) Cis-octahydro-1H-quinolin-2-one

One gram of platinum(IV) oxide was added to a solution of 80 g of 3,4,5,6,7,8-hexahydro-1H-quinolin-2-one and this was hydrogenated at 20° to 25° C. under normal pressure. After filtration of the reaction solution, it was evaporated and the residue was fractionally crystallized from n-hexane. 35 g of cis-octahydro-1H-quinolin-2-one having a melting point of 123° to 126° C. were obtained.

(c) 3,3-Dichloro-cis-octahydro-1H-quinolin-2-one 28.8 g of phosphorus pentachloride were added to a solution of 23 g of cis-octahydro-1H-quinolin-2-one in 350 ml of anhydrous chloroform. To this were added dropwise 43.1 g of sulfuryl chloride in 45 ml of anhydrous chloroform at 20° to 30° C. within 30 min and the reaction mixture was stirred at the boiling point for 5 hours. After allowing to stand overnight, the mixture was neutralized with aqueous potassium carbonate cooled to 0° C. The aqueous phase was extracted twice with methylene chloride. The combined organic phases were dried over sodium sulfate and concentrated. The residue was recrystallized from ethanol with the addition of active charcoal. 32 g of pale yellow crystals, having a melting point of 176° to 177° C., were obtained.

(d) 3-Chloro-cis-octahydro-1H-quinolin-2-one 15.9 g of 3,3-dichloro-cis-octahydro-1H-quinolin-2-one in one liter of ethanol, with the addition of 10 ml of triethylamine and Raney nickel, were hydrogenated at 20° to 25° C. under normal pressure until one mole-equivalent had been taken up. After filtration, the solution was evaporated, the residue was taken up in ethyl acetate, the solution was extracted twice with water and dried over sodium sulfate. After removal of the solvent, the product was triturated with diisopropyl ether and filtered off with suction. Colorless crystals, having a melting point of 185° C., were obtained.

(e) 2β,3aβ,7aβ-Octahydroindole-2-carboxylic acid 3.75 g of 3-chloro-cis-octahydro-1H-quinolin-2-one were added to a boiling solution of 6.63 g of barium hydroxide octahydrate in 120 ml of water. After heating under reflux for 3.5 hours, 0.9 ml of concentrated sulfuric acid was added to the reaction mixture and this was heated to boiling for a further hour and then allowed to stand overnight.

The precipitate was filtered off with suction and the filtrate was adjusted to a pH of 6.5 with 1N sodium hydroxide and evaporated to dryness. The residue was extracted with boiling ethanol, concentrated and induced to crystallize.

Yield: 3.1 g.

The compounds 2β-cis-octahydrocyclopenta[b]pyrrole-2-carboxylic acid (corresponds to the compound from Example 2 (d) and 2β,3aβ,8aβ-decahydrocyclohepta[b]pyrrole-2-carboxylic acid (corresponds to the compound in Example 3 (d) may be prepared in a manner analogous to that described in Example 4.

EXAMPLE 5

Benzyl 2β,3aβ,7aβ-octahydroindole-2-carboxylate hydrochloride 3 ml of thionyl chloride were added dropwise to 25 ml of benzyl alcohol. 3 g of 2β,3aβ,7aβ-octahydroindole-2-carboxylic acid hydrochloride were added to this mixture. The reaction mixture was allowed to stand at 5° C. for 2 days, after which a clear solution had formed. After evaporation, diisopropyl ether was added to the residue obtained and this was filtered off with suction. 3.8 g of the title compound, having a melting point of 150° C. (with decomposition), were obtained.

The following ester compounds in Examples 6 and 7 may be prepared in a manner analogous to that described in Example 5:

EXAMPLE 6

Benzyl 2β,3aβ,6aβ-octahydrocyclopenta[b]pyrrole-2-carboxylate hydrochloride $^1$H NMR data: 1.0–2.3 (m, 9H); 3.4–3.9 (m, 1H); 4.1–4.6 (m, 1H); 5.1 (s, 2H); 7.2 (s, 5H).

EXAMPLE 7

Benzyl 2β,3aβ,8aβ-decahydrocyclohepta[b]pyrrole-2-carboxylate hydrochloride $^1$H NMR data: 0.9–2.3 (m, 13H); 3.5–3.9 (m, 1H); 4.2–4.7 (m, 1H); 5.2 (s, 2H); 7.2 (s, 5H).

EXAMPLE 8

Tert.-butyl 2β,3aβ,7aβ-octahydroindole-2-carboxylate hydrochloride 10 ml of concentrated sulfuric acid and 50 g of isobutylene were added to a solution of 10 g of 2β,3aβ,7aβ-octahydroindole-2-carboxylic acid in 100 ml of dioxane cooled down to −10° C. The reaction mixture was slowly warmed to 20° to 25° C. in an autoclave and stirred at this temperature for 20 hours.

The mixture was added to ice-cold 50% strength aqueous sodium hydroxide and extracted with methylene chloride. The combined organic phases were washed with water, dried with sodium sulfate and concentrated. The residue was taken up in ether and the pH was adjusted to 2.0 to 3.0 by means of ethereal hydrogen chloride. The mixture was evaporated to dryness and the product was triturated with diisopropyl ether. 7.3 g of the title compound were obtained after filtering off with suction.

$^1$H NMR data: 1.0–2.5 (m, 11H); 1.3 (s, 9H); 3.4–3.9 (m, 1H); 4.0–4.5 (m, 1H).

The following ester compounds of Examples 9 and 10 can be prepared in analogy to the procedure described in Example 8:

EXAMPLE 9

Tert.-butyl 2β,3aβ,6aβ-octahydrocyclopenta[b]pyrrole-2-carboxylate hydrochloride $^1$H NMR data: 1.0–2.7 (m, 9H); 1.3 (s, 9H); 3.4–3.9 (m, 1H); 4.0–4.5 (m, 1H).

EXAMPLE 10

Tert.-butyl 2β,3aβ,8aβ-decahydrocyclohepta[b]pyrrole-3-carboxylate hydrochloride $^1$H NMR data: 0.8–2.9 (m, 13H); 1.3 (s, 9H); 3.4–3.9 (m, 1H); 4.0–4.5 (m, 1H).

EXAMPLE 11

Benzyl N-(1S-carboethoxy-3-phenylpropyl)-S-alanyl-2S,3aR,-7aR-octahydroindole-2-carboxylate (=diastereomer A11) and benzyl N-(1S-carboethoxy-3-phenylpropyl)-S-alanyl-2R,3aS,-7aS-octahydroindole-2-carboxylate (=diastereomer B 11)

2.5 g of N-(1S-carboethoxy-3-phenylpropyl)-S-alanine, 1.22 g of 1-hydroxybenzotriazole, 2.5 g of benzyl (d,1)-2β,3aβ,7aβ-octahydroindole-2-carboxylate hydrochloride, 1.25 ml of N-ethylmorpholine and 2 g of dicyclohexylcarbodiimide were added to 20 ml of dimethylformamide at 0° C.

The mixture was stirred at 0° C. for 1 hour, then slowly warmed to room temperature and stirred at 20° to 25° C. overnight.

25 ml of ethyl acetate were added to the reaction mixture and precipitated urea was filtered off with suction. After evaporation of the solution, the residue obtained was taken up in 50 ml of ether, the ethereal solution was washed with saturated aqueous sodium bicarbonate and water, dried and concentrated. A mixture of the abovementioned diastereomers A 11 and B 11 was obtained which was separated over silica gel using a mixture of cyclohexane and ethyl acetate (4:1).

$R_f$ value for diastereomer A 11:0.36;
$R_f$ value for diastereomer B 11:0.34.

The following compounds in Examples 12 to 16 were obtained in a procedure analogous to that described in Example 11.

EXAMPLE 12

Tert.-butyl N-(1S-carboethoxy-3-phenylpropyl)-S-alanyl-2S,3aR,-7aR-octahydroindole-2-carboxylate (=diastereomer A 12)

$^1$H NMR data: 1.25 (d+t, 6H); 1.35 (s, 9H); 1.3–3.6 (m, 18H); 4.2 (q, 2H); 4.4 (m, 1H); 7.3 (s, 5H).

EXAMPLE 13

Benzyl N-(1S-carboethoxy-3-phenylpropyl)-S-alanyl-2S,3aR,-6aR-octahydrocyclopenta[b]pyrrole-2-carboxylate (=diastereomer A 13)

$^1$H NMR data: 1.1 (d, 3H); 1.3 (t, 3H); 1.3–2.4 (m, 10H); 2.3–3.4 (m, 6H); 4.1 (q, 2H); 4.55 (d, 1H); 5.2 (s, 2H); 7.2 (s, 5H); 7.4 (s, 5H).

EXAMPLE 14

Benzyl N-(1S-carboethoxy-3-phenylpropyl)-S-alanyl-2S,3aR,-8aR-decahydrocyclohepta[b]pyrrole-2-carboxylate (=diastereomer A 14)

$^1$H NMR data: 1.2 (d+t, 6H); 1.3–2.4 (m, 14H); 2.3–3.4 (m, 6H); 4.2 (q, 2H); 4.6 (m, 1H); 5.2 (s, 2H); 7.25 (s, 5H); 7.4 (s, 5H).

EXAMPLE 15

Tert.-butyl
N-(1S-carboethoxy-3-phenylpropyl)-S-alanyl-2S,3aR,-6aR-octahydrocyclopenta[b]pyrrole-2-carboxylate
(=diastereomer A 15)

$^1$H NMR data: 1.1 (d, 3H); 1.3 (t, 3H); 1.3–2.4 (m, 10H); 1.4 (s, 9H); 2.3–3.4 (m, 6H); 4.2 (q, 2H); 4.6 (m, 1H); 7.2 (s, 5H).

EXAMPLE 16

Tert.-butyl
N-(1S-carboethoxy-3-phenylpropyl)-S-alanyl-2S,3aR,-8aR-decahydrocyclohepta[b]pyrrole-2-carboxylate
(=diastereomer A 16)

$^1$H NMR data: 1.1 (d, 3H); 1.3 (t, 3H); 1.4 (s, 9H); 1.4–2.5 (m, 14H); 2.3–3.4 (m, 6H); 4.1 (q, 2H); 4.7 (m, 1H); 7.3 (s, 5H).

EXAMPLE 17

N-(1S-Carboethoxy-3-phenylpropyl)-S-alanyl-2S,3aR,-7aR-octahydroindole-2-carboxylic acid hydrochloride

Method A 0.7 g of diastereomer A 11 from Example 11 were hydrogenated in 25 ml of ethanol with 100 ml of palladium-animal charcoal (10%) at 20° to 25° C. under normal pressure. After removal of the catalyst, the solution was treated with 0.5N ethanolic hydrogen chloride until the reaction was acid. The solution was concentrated in vacuo and the residue was triturated with diisopropyl ether. 400 mg of the title compound, having a melting point of 198° to 200° C., were obtained.

$^1$H NMR data of the free base: 1.0–3.0 (m, 19H); 3.0–3.3 (t, 1H); 3.3–3.9 (m, 3H); 3.9–4.4 (q, 2H); 4.4–4.7 (broad s, 4H); 7.2 (s, 5H).

Method B

A solution of 0.8 g of diastereomer A 12 from Example 12 in 5 ml of methylene chloride was saturated with dry hydrogen chloride gas and allowed to stand at 20 to 25° C. for 16 hours. The solution was concentrated in vacuo, the residue was triturated with diisopropyl ether and filtered off with suction.

Yield: 550 mg.

EXAMPLE 18

N-(1S-Carboethoxy-3-phenylpropyl)-S-alanyl-2S,3aR,-6aR-octahydrocyclopenta[b]pyrrole-2-carboxylic acid hydrochloride This compound was obtained from the diastereomer A 13 in Example 13 in a procedure analogous to method A in Example 17.

$^1$H NMR data: 1.2 (d, 3H); 1.3 (t, 3H); 1.2–3.8 (m, 16H); 4.15 (q, 2H); 4.2–4.6 (m, 4H); 7.2 (s, 5H).

EXAMPLE 19

N-(1S-Carboethoxy-3-phenylpropyl)-S-alanyl-2S,3aR,-8aR-decahydrocyclohepta[b]pyrrole-2-carboxylic acid hydrochloride This compound was prepared from diastereomer A 14 in Example 14 in analogy to the method A described in Example 17.

$^1$H NMR data: 1.2 (d, 3H); 1.3 (t, 3H); 1.2–3.8 (m, 20H); 4.2 (q, 2H); 4.0–4.7 (m, 4H); 7.2 (s, 5H).

The compounds of Examples 18 and 19 can also be prepared from the diastereomers A 15 and A 16 respectively by the method B described in Example 17.

EXAMPLE 20

N-(1S-Carboxy-3-phenylpropyl)-S-alanyl-2S,3aR,7aR-octahydroindole-2-carboxylic acid Two equivalents of potassium hydroxide and a 10% excess of 4N potassium hydroxide were added to a solution of 1 g of N-(1S-carboethoxy-3-phenylpropyl)-S-alanyl-2S,3aR,7aR-octahydroindole-2-carboxylic acid hydrochloride in 10 ml of water. After stirring for 8 hours at 20° to 25° C., the reaction solution was adjusted to a pH of 4.0 with 2N hydrochloric acid and concentrated in vacuo. The residue was taken up in ethyl acetate and precipitated salt was filtered off. The ethyl acetate solution was concentrated and the residue was triturated with diisopropyl ether and filtered off with suction.

Yield: 0.6 g.

$^1$H NMR data: 1.2 (d, 3H); 1.2–3.8 (m, 18H); 4.0–4.6 (m, 4H); 7.2 (s, 5H).

EXAMPLE 21

N-(1S-Carboxy-3-phenylpropyl)-S-alanyl-2S,3aR,6aR-octahydrocyclopenta[b]pyrrole-2-carboxylic acid This compound was prepared from the compound in Example 18 in analogy to the process described in Example 20.

$^1$H NMR data: 1.2 (d, 3H); 1.2–3.8 (m, 16H); 4.05–4.7 (m, 4H); 7.2 (s, 5H).

EXAMPLE 22

N-(1S-Carboxy-3-phenylpropyl)-S-alanyl-2S,3aR,8aR-decahydrocyclohepta[b]pyrrole-2-carboxylic acid This compound was prepared from the compound in Example 19 in analogy to the process described in Example 20.

$^1$H NMR data: 1.2 (d, 3H); 1.3–3.9 (m, 20H); 4.0–4.7 (m, 4H); 7.2 (s, 5H).

EXAMPLES 23

Tert.-butyl
N-(1S-carboethoxy-3-phenyl-3-oxopropyl)-S-alanyl-2β,3aβ,7aβ-octahydroindole-2-carboxylate 2.5 g of N-(1S-carboethoxy-3-phenyl-3-oxopropyl)-S-alanine, together with 1.2 g of 1-hydroxybenzotriazole, 2.5 g of tert.-butyl (d,l )2β,3aβ,7aβ-octahydroindole-2-carboxylate hydrochloride, 1.25 ml of N-ethylmorpholine and 2 g of dicyclohexylcarbodiimide, were added to 20 ml of dimethylformamide. The mixture was stirred at 0° C. for 1 hour and then at 20° to 25° C. for 12 hours.

The reaction solution was diluted with 25 ml of ethyl acetate and precipitated urea was filtered off with suction. After concentration in vacuo, the residue obtained was taken up in ether, the ethereal solution was washed with saturated aqueous sodium bicarbonate and with water, dried and evaporated. 3 g of the title compound were obtained as a mixture of diastereomers.

$^1$H NMR data: 1.2 (s, 9H); 0.9–2.6 (m, 18H); 3.5–5.1 (m, 6H); 7.2–8.2 (m, 5H).

The mixture of diastereomers can be separated over silica gel into the optically pure compounds using cyclohexane/ethyl acetate as the eluant.

EXAMPLES 24 to 28

The following compounds of Examples 24 to 28 may be prepared in a procedure analogous to Example 23 using the appropriate bicyclic carboxylic acid ester compounds.

EXAMPLE 24

Tert.-butyl N-(1S-carboethoxy-3-phenyl-3-oxopropyl)-S-alanyl-2β,3aβ,6aβ-octahydrocyclopenta[b]pyrrole-2-carboxylate $^1$H NMR data: 1.2 (s, 9H); 0.9-2.5 (m, 16H); 3.5-5.1 (m, 6H); 7.2-8.2 (m, 5H).

EXAMPLE 25

Tert.-butyl N-(1S-carboethoxy-3-phenyl-3-oxopropyl)-S-alanyl-2S,3aR,8aR-decahydrocyclohepta[b]pyrrole-2-carboxylate $^1$H NMR data: 1.4 (s, 9H); 1.0-2.8 (m, 20H); 3.4-5.1 (m, 6H); 7.2-8.2 (m, 5H).

EXAMPLE 26

Benzyl N-(1S-carboethoxy-3-phenyl-3-oxopropyl)-S-alanyl-2β,3aβ,7aβ-octahydroindole-2-carboxylate $^1$H NMR data: 1.2 (d, 3H); 1.3 (t, 3H); 1.4-2.4 (m, 10H); 2.4-3.9 (m, 6H); 4.2 (q, 2H); 4.3-4.8 (m, 1H); 5.2 (s, 2H); 7.2 (s, 5H); 7.4-8.0 (m, 5H).

EXAMPLE 27

Benzyl N-(1S-carboethoxy-3-phenyl-3-oxopropyl)-S-alanyl-2β,3aβ,6aβ-octahydrocyclopenta[b]pyrrole-2-carboxylate $^1$H NMR data: 1.25 (d+t, 6H); 1.4-2.4 (m, 8H); 2.4-3.8 (m, 6H); 4.2 (q, 2H); 4.3-4.8 (m, 1H); 5.2 (s, 2H); 7.2 (s, 5H); 7.4-8.0 (m, 5H).

EXAMPLE 28

Benzyl N-(1S-carboethoxy-3-phenyl-3-oxopropyl)-S-alanyl-2β,3aβ,8aβ-decahydrocyclohepta[b]pyrrole-2-carboxylate $^1$H NMR data: 1.2 (d, 3H); 1.3 (t, 3H); 1.4-2.5 (m, 12H); 2.4-3.8 (m, 6H); 4.2 (q, 2H); 4.3-4.8 (m, 1H); 5.2 (s, 2H); 7.2 (s, 5H); 7.4-8.0 (m, 5H).

EXAMPLE 29

N-(1S-Carboethoxy-3-phenyl-3-oxopropyl)-S-alanyl-2β,3aβ,7aβ-octahydroindole-2-carboxylic acid trifluoroacetate 2.6 g of the mixture of diastereomers from Example 23 were stirred in 15 ml of trifluoroacetic acid at 20° to 25° C. for 2 hours. The solution was concentrated in vacuo, the residue was triturated with diisopropyl ether and filtered off with suction.

Yield: 0.8 g.

$^1$H NMR data: 1.2 (d+t, 6H); 1.3-3.6 (m, 16H); 4.2 (q, 2H); 4.1-4.6 (m, 4H); 7.3-8.1 (m, 5H).

EXAMPLE 30

N-(1S-Carboethoxy-3-phenyl-3-oxopropyl)-S-alanyl-2β,3aβ,6aβ-octahydrocyclopenta[b]pyrrole-2-carboxylic acid trifluoroacetate This compound was prepared in analogy to the procedure described in Example 29.

$^1$H NMR data: 1.2 (d+t, 6H); 1.3-3.6 (m, 14H); 4.15 (q, 2H); 4.0-4.6 (m, 4H); 7.3-8.0 (m, 5H).

EXAMPLE 31

N-(1S-Carboethoxy-3-phenyl-3-oxopropyl)-S-alanyl-2β,3aβ,8aβ-decahydrocyclohepta[b]pyrrole-2-carboxylic acid 1 g of tert.-butyl N-(1S-carboethoxy-3-phenyl-3-oxopropyl)-S-alanyl-2β,3aβ,8aβ-decahydrocyclohepta[b]pyrrole-2-carboxylate was dissolved in 10 ml of methylene chloride, the solution was saturated with hydrogen chloride gas and allowed to stand at 20° to 25° C. for 16 hours. The solution was concentrated in vacuo and the residue was triturated with diisopropyl ether and filtered off with suction.

Yield: 0.4 g.

$^1$H NMR data: 1.3 (d+t, 6H); 1.3-3.8 (m, 18H); 4.2 (q, 2H); 4.0-4.7 (m, 4H); 7.2-8.1 (m, 5H).

The carboxylic acids described in the foregoing Examples 29 to 31 can also be prepared from the corresponding benzyl esters by catalytic hydrogenolysis (10% palladium on charcoal, ethanol, 20° to 25° C.).

EXAMPLE 32

N-(1S-Carboxy-3-phenyl-3-oxopropyl)-S-alanyl-2β,3aβ,7aβ-octahydroindole-2-carboxylic acid For the preparation of this compound, 1 g of N-(1S-carboethoxy-3-phenyl-3-oxopropyl)-S-alanyl-2β,3aβ,7aβ-octahydroindole-2-carboxylic acid was reacted with potassium hydroxide in analogy to the procedure described in Example 19.

$^1$H NMR data: 1.2 (d, 3H); 1.3-3.6 (m, 16H); 4.1-4.7 (m, 4H); 7.2-8.1 (m, 5H).

EXAMPLE 33

N-(1S-Carboethoxy-3-phenyl-3-hydroxypropyl)-S-alanyl-2β,3aβ,7aβ-octahydroindole-2-carboxylic acid 1 g of N-(1S-carboethoxy-3-phenyl-3-oxopropyl)-S-alanyl-2β,3aβ,7aβ-octahydroindole-2-carboxylic acid was dissolved in 50 ml of anhydrous ethanol and hydrogenated with 1 mole equivalent of hydrogen and 50 mg of palladium/charcoal at 20° to 25° C. under normal pressure. After removal of the catalyst by filtration, the solution was evaporated and the residue was triturated with diisopropyl ether and filtered off with suction.

Yield: 0.7 g.

$^1$H NMR data: 1.2 (d, 3H); 1.3 (t, 3H); 1.3-3.8 (m, 16H); 4.2 (q, 2H); 4.1-4.6 (m, 4H); 4.7 (d, 1H); 7.1-7.4 (m, 5H).

EXAMPLE 34

N-(1S-Carboethoxy-3-phenyl-3-hydroxypropyl)-S-alanyl-2β,3aβ,6aβ-octahydrocyclopenta[b]pyrrole-2-carboxylic acid This compound was prepared according to the procedure described in Example 33 from the compound described in Example 29.

$^1$H NMR data: 1.2 (d, 3H); 1.3 (t, 3H); 1.4–3.9 (m, 14H); 4.2 (q, 2H); 4.1–4.7 (m, 4H); 4.7 (d, 1H); 7.0–7.4 (m, 5H).

EXAMPLE 35

N-(1S-Carboethoxy-3-phenyl-3-hydroxypropyl)-S-alanyl-2β,3aβ,8aβ-decahydrocyclohepta[b]pyrrole-2-carboxylic acid This compound was prepared according to the procedure described in Example 33 from the compound described in Example 31.

$^1$H NMR data: 1.25 (d+t, 6H); 1.3–4.0 (m, 18H); 4.2 (q, 2H); 4.1–4.6 (m, 4H); 4.8 (d, 1H); 7.0–7.5 (m, 5H).

EXAMPLE 36

Benzyl S-alanyl-2S,3aR,7aR-octahydroindole-2-carboxylate (a) Benzyl N-tert.-butoxycarbonyl-S-alanyl-2S,3aR,7aR-octahydroindole-2-carboxylate 13 ml of N-ethylmorpholine, 13.5 g of 1-hydroxybenzotriazole and 29.6 g of benzyl 2β,3aβ,7aβ-octahydroindole-2-carboxylate hydrochloride were added to a solution of 19 g of Boc-Ala-OH in 100 ml of DMF. The mixture was cooled in an ice bath and 21 g of dicyclohexylcarbodiimide were added. The mixture was stirred at 20° to 25° C. for 15 hours. The precipitated urea was filtered off with suction, the filtrate was evaporated in vacuo and taken up in ethyl acetate. The organic phase was extracted 3 times in each case with aqueous potassium bisulfate, potassium bicarbonate and sodium chloride, dried and concentrated. The residue was chromatographed on silica gel with ethyl acetate/cyclohexane (1:3). The first fraction contained the desired product.

Yield: 21 g.

$^1$H NMR data: 1.3 (d, 3H); 1.45 (s, 9H); 1.1–2.4 (m, 12H); 3.2–3.9 (m, 2H); 5.3 (s, 2H); 7.4 (s, 5H).

(b) Benzyl S-alanyl-2S,3aR,7aR -octahydroindole-2-carboxylate 20.5 g of benzyl N-tert.-butoxycarbonyl-S-alanyl-2S,3aR,7aR-octahydroindole-2-carboxylate were dissolved in 50 ml of trifluoroacetic acid. After a reaction time of 10 min., the solution was concentrated in vacuo, and the residue was triturated several time with diisopropyl ether and then dried in vacuo.

Yield: 14 g.

EXAMPLES 37 and 38;

These compounds were prepared in analogy to the procedures described in Example 36 under (a) and (b).

EXAMPLE 37

Benzyl S-alanyl-2S,3aR,6aR-octahydrocyclopenta[b]pyrrole-2-carboxylate $^1$H NMR data: 1.3 (d, 3H); 1.1–2.4 (m, 10H); 3.2–3.9 (m, 2H); 5.2 (s, 2H); 7.4 (s, 5H).

EXAMPLE 38

Benzyl S-alanyl-2S,3aR,8aR -decahydrocyclopenta[b]pyrrole-2-carboxylate $^1$H NMR data: 1.3 (d, 3H); 1.1–2.4 (m, 14H); 3.2–3.9 (m, 2H); 5.2 (s, 2H); 7.4 (s, 5H).

EXAMPLE 39

N-(1S-Carboethoxy-3-phenylpropyl)-S-alanyl-2S.3aR,-7aR-octahydroindole-2-carboxylic acid (a) Benzyl N-(1S-carboethoxy-3-phenylpropyl)-S-alanyl-2S,3aR,-7aR-octahydroindole-2-carboxylate 10 mmoles of benzyl S-alanyl-2S,3aR,7aR-octahydroindole-2-carboxylate were dissolved in 30 ml of anhydrous ethanol. The solution was adjusted to a pH of 7.0 by means of ethanolic potassium hydroxide and 1 g of powdered molecular sieve (4 Å) and then 10 mmoles of ethyl 2-keto-4-phenylbutyrate were added. A solution of 1 g of sodium cyanoborohydride in 10 ml of anhydrous ethanol was slowly added dropwise. After a reaction time of 20 hours at 20° to 25° C., the reaction solution was filtered and the solvent was distilled off. The residue was taken up in ethyl acetate/water. After concentration of the ethyl acetate phase, the residue was chromatographed on silica gel with ethyl acetate/cyclohexane (1:4). The $^1$H NMR data agree with the data of the compound from Example 11.

(b) The compound obtained above was reacted further as described in Example 17, method A to give the desired compound.

EXAMPLE 40

Benzyl N-(1S-carboethoxy-3-oxo-3-phenylpropyl)-S-alanyl-2β,3aβ,6aβ-octahydrocyclopenta[b]pyrrole-2-carboxylate 10 mmoles of benzyl S-alanyl-2S,3aR,6aR-octahydrocyclopenta[b]pyrrole-2-carboxylate were dissolved in 100 ml of anhydrous ethanol together with 10 mmoles of ethyl 3-benzoylacrylate and 10 mmoles of triethylamine and the mixture was stirred at 20° to 25° C. for 24 hours. It was then neutralized with 1N hydrochloric acid, evaporated to dryness and the residue was taken up with ethyl acetate/water. The ethyl acetate phase was dried, evaporated and chromatographed on silica gel.

EXAMPLE 41

Benzyl N-(1S-carboethoxy-3-oxo-3-phenylpropyl)-S-alanyl- 2β,3aβ,8aβ-decahydrocyclopenta[b]pyrrole-2-carboxylate 10 mmoles of acetophenone, 10 mmoles of ethyl glyoxylate and 10 mmoles of benzyl S-alanyl-2S,3aR,-8aR-decahydrocyclohepta[b]pyrrole-2-carboxylate were heated at 45° C. in 30 ml of glacial acetic acid for 36 hours. After concentration in vacuo, the mixture was made alkaline with aqueous sodium bicarbonate and extracted with ethyl acetate. The ethyl acetate phase was concentrated and chromatographed on silica gel.

EXAMPLE 42

N-(1S-Carboethoxy-3-phenylpropyl)-S-alanyl-2S,3aR,-7aS-octahydroindole-2-carboxylic acid (a) Benzyl DL-2β,3aβ,7aα, -octahydroindole-2-carboxylate hydrochloride 1.4 g of DL-2β,3aβ,7aα-octahydroindole-2-carboxylic acid were added, at −10° to 0° C., to a solution of 1.4 ml of thionyl chloride in 14 ml of benzyl alcohol prepared at −5° to 0° C. The mixture was stirred at 0° C.

for 1 hour and was then allowed to stand overnight at 20° to 25° C. The benzyl alcohol was distilled off at 50° C. under high vacuum and the residue was triturated with diisopropyl ether, 2.5 g of colorless crystals, of m.p. 154° C., were obtained.

(b) Benzyl N-(1S-carboethoxy-3-phenylpropyl)-S-alanyl-2β,3aβ,-7aα-octahydroindole-2-carboxylate 1.06 g of 1-hydroxybenzotriazole, 2.2 g of benzyl DL-2β,3aβ,7aα-octahydroindole-2-carboxylate hydrochloride and 1.08 ml of N-ethylmorpholine were added to a suspension of 2.16 g of N-(1S-carboethoxy-3-phenylpropyl)-S-alanine in 8.6 ml of anhydrous dimethylformamide and then 1.7 g of dicyclohexylcarbodiimide were added at 0° C. After stirring at 20° to 25° C. for 3.5 hours, the reaction mixture was diluted with 20 ml of ethyl acetate and the precipitated dicyclohexylurea was filtered off. After concentration in vacuo, the residue was taken up in ether, washed twice with saturated aquous sodium bicarbonate, dried over sodium sulfate and evaporated. After chromatography on silica gel using ethyl acetate-cyclohexane as the eluant, 2 pale yellow oils were obtained in the ratio 1:1, and these each contain one isomer of the desired compound.

$^1$H NMR data of the isomer having the 2R,3aR,7aS configuration: 7.35 (s, 5H); 7.2 (s, 5H); 5.18 (s, 2H); 4.55 (d, 1H); 4.1 (q, 2H); 3.4–2.3 (m, 6H); 2.4–1.3 (m, 12H); 1.3 (t, 3H); 1.1 (d, 3H).

$^1$H NMR data of the isomer having the 2S,3aS,7aR configuration: 7.35 (s, 5H); 7.2 (s, 5H); 5.16 (s, 2H); 4.9–4.2 (m, 1H); 4.2 (q, 2H); 3.9–2.4 (m, 6H); 2.4–1.4 (m, 12H); 1.25 (d+t, 6H).

(c) N-(1S-Carboethoxy-3-phenylpropyl)-S-alanyl-2S,3aR,-7aS-octahydroindole-2-carboxylic acid 1.7 g of the isomer having the 2S,3aS,7aR configuration obtained under (b) were hydrogenated under normal pressure in 60 ml of anhydrous ethanol with the addition of 200 mg of palladium-charcoal (10%) at 20° to 25° C. for 2 hours. The catalyst was filtered off and the filtrate was evaporated. 1.2 g of the title compound were obtained as a colorless foam.

$^1$H NMR data: 7.2 (s, 5H); 4.4 (m, 4H); 4.2 (q, 2H); 3.6–1.3 (m, 18H); 1.28 (d+t, 6H).

The hydrochloride of the abovementioned compound was obtained as a colorless amorphous powder.

EXAMPLES 43 to 47

The compounds mentioned in these examples were prepared in analogy to the procedures described in Example 42.

EXAMPLE 43

N-(1S-Carboethoxy-3-phenylpropyl)-S-alanyl-2S,3aS,-7aR-octahydroindole-2-carboxylic acid This compound was obtained from the mixture of products from Example 51, which were further reacted according to the procedure of Example 42. The isomers were separated by column chromatography on silica gel before hydrogenation in accordance with Example 42c.

$^1$H NMR data: 7.2 (s, 5H); 4.0–4.6 (m, 4H); 4.15 (q, 2H); 3.8–1.2 (m, 18H); 1.3 (t, 3H); 1.2 (d, 3H).

The hydrochloride was obtained as a colorless amorphous powder.

EXAMPLE 44

N-(1S-Carboethoxy-3-phenylpropyl)-S-alanyl-2S,3aR,-6aS-octahydrocyclopenta[b]pyrrole-2-carboxylic acid $^1$H NMR data: 7.25 (s, 5H); 4.35 (m, 4H); 4.2 (q, 2H); 3.9–1.4 (m, 16H); 1.35 (t, 3H); 1.15 (d, 3H).

The hydrochloride was obtained as a colorless amorphous powder.

EXAMPLE 45

N-(1S-Carboethoxy-3-phenylpropyl)-S-alanyl-2S,3aS,-6aR-octahydrocyclopenta[b]pyrrole-2-carboxylic acid $^1$H NMR data: 7.3 (s, 5H); 4.3 (m, 4H); 4.2 (q, 2H); 3.8–1.3 (m, 16H); 1.3 (t+d, 6H).

The hydrochloride was obtained as a colorless amorphous powder.

EXAMPLE 46

N-(1S-Carboethoxy-3-phenylpropyl)-S-alanyl-2S,3aR,-8aS-decahydrocyclohepta[b]pyrrole-2-carboxylic acid $^1$H NMR data: 7.15 (s, 5H); 4.4 (m, 4H); 4.2 (q, 2H); 3.8–1.3 (m, 20H); 1.3 (t+d, 6H).

EXAMPLE 47

N-(1S-Carboethoxy-3-phenylpropyl)-S-alanyl-2S,3aS,-8aR-decahydrocyclohepta[b]pyrrole-2-carboxylic acid $^1$H NMR data: 7.2 (s, 5H); 4.4 (m, 4H); 4.25 (q, 2H); 3.8–1.2 (m, 20H); 1.3 (t, 3H); 1.15 (d, 3H).

EXAMPLE 48

2β,3aβ,7aα-Octahydroindolecarboxylic acid (a) Methyl 3-chloro-N-acetylalanine 181 g of methyl 3-chloroalanine hydrochloride were heated under reflux with 163.9 g of acetyl chloride in 1.5 l of anhydrous toluene for about 5 hours until a clear solution was obtained. This was evaporated to dryness and the residue was crystallized from ethyl acetate/petroleum ether. 170 g of product of m.p. 104° C. were obtained.

(b) Methyl 3-(2-oxocyclohexyl)-N-acetylalanine 160 g of methyl 3-chloro-N-acetylalanine and 171.9 g of 1-pyrrolidinocyclohexene were dissolved in 1.2 l of absolute DMF and the mixture was allowed to stand at 20° to 25° C. for 3 days.

The solution was concentrated under high vacuum, the residue obtained was taken up in 600 ml of water and the pH was adjusted to 2.0 with concentrated hydrochloric acid. The aqueous solution was extracted with ethyl acetate and the organic phase was dried over sodium sulfate and evaporated. The product was obtained as a yellow oil.

(c) 3,3a,4,5,6,7-2H-Hexahydroindole-2-carboxylic acid hydrochloride 220 g of the compound obtained under (b) were heated to boiling under reflux with 1 l of 2N of hydrochloric acid for 2 hours. The reaction mixture was extracted with ethyl acetate and the aqueous phase was concentrated. Residual amounts of water were removed by evaporation in vacuo with the addition of toluene three times. 210 g of the product were obtained as a yellow oil which crystallized on being left to stand.

(d) 2β,3aβ,7aα-Octahydroindole-2-carboxylic acid 128 g of 3,3a,4,5,6,7-2H-hexahydroindole-2-carboxylic acid hydrochloride were hydrogenated under normal pressure in 700 ml of glacial acetic acid with the addition of 4 g of platinum/charcoal (10%) at room temperature. The catalyst was filtered off and the filtrated was evaporated to dryness. The residue was dissolved in 500 ml of hot ethanol and cooled down to −20° C. This caused the 2β,3aβ,7aβ-isomer of the title compound to precipitate out. The product was obtained from the solution by concentrating and adding isopropanol, in the form of colorless crystals of m.p. 280° C.

EXAMPLE 49

2β, 3aβ,8aα-Decahydrocyclohepta[b]pyrrole-2-carboxylic acid

This compound was prepared in analogy to the procedures (b) to (d) of Example 48 starting from pyrrolidinocycloheptene.

EXAMPLE 50

2β,3aβ,6aα-Octahydrocyclopenta[b]pyrrole-2-carboxylic acid

This compound was prepared in analogy to the procedures (b) to (d) of Example 48, starting from pyrrolidinocyclopentene.

EXAMPLE 51

2β,3aα,7aβ-Octahydroindole-2-carboxylic acid (a) 3,4,5,6,7,8-Octahydro-1H-quinolin-2-one 392 g of cyclohexanone and 212 g of acrylonitrile, together with 20 g of cyclohexylamine, 4 g of glacial acetic acid and 0.4 g of hydroquinone, were heated under reflux for 4 hours up to a final temperature of 200° C. The distillate obtained after distillation at 100° to 150° C./0.5 mm Hg was heated with 10 ml of 50% strength acetic acid at 200° C. for 2 days. After cooling down, the reaction mixture was recrystallized from methanol/water. Combined with the residue from distillation, obtained previously, which was recrystallized from n-hexane, 460 g of the product of m.p. 143° to 144° C. were obtained.

(b) Trans-octahydro-1H-quinolin-2-one

A mixture of 25 g of the product obtained under (a) and 70 g of sodium formate in 120 ml of formic acid were heated to boiling under reflux for 18 hours. The reaction solution was made alkaline with 20% strength aqueous sodium hydroxide and extracted with ethyl acetate. The organic phase was dried over sodium sulfate and concentrated. The residue was recrystallized from cyclohexane and the product was obtained having an m.p. of 152° C.

(c) 3,3-Dichloro-trans-octahydro-1H-quinoline-2-one

A solution of 36.4 g of sulfuryl chloride in 40 ml of chloroform was added dropwise at 20° to 30° C. over 30 minutes to a solution of 19.4 g of the compound obtained under (b) and 24.3 g of phosphorus pentachloride in 300 ml of anhydrous chloroform. The mixture was heated to boiling for 6 hours and allowed to stand overnight at 20° to 25° C.

The mixture was neutralized with ice-cold saturated aqueous potassium carbonate, extracted with methylene chloride, and the organic phase was dried over sodium sulfate and then concentrated. After recrystallization of the product from ethanol, with the addition of active charcoal, 25 g of the product, of m.p. 195° to 198° C., were obtained.

(d) 3-Chloro-trans-octahydro-1H-quinolin-2-one 15.6 g of the compound obtained under (c) were hydrogenated under normal pressure in 1 l of ethanol and 9.7 ml of triethylamine, with the addition of Raney nickel, at 20° to 25° C. until 1 mole-equivalent of hydrogen had been taken up.

After the catalyst had been filtered off, the filtrate was evaporated to dryness and the residue was taken up in ethyl acetate. The organic phase was washed twice with water, dried over sodium sulfate and evaporated. The residue was triturated with diisopropyl ether, filtered off with suction and dried. The product was obtained in the form of pale yellow crystals of m.p. 115°–120° C.

(e) 2β,3aα,7aβ-Octahydroindole-2-carboxylic acid 3.75 g of the compound obtained under (d) were added to a boiling solution of 6.63 g of barium hydroxide octahydrate in 120 ml of water. After heating under reflux for 4 hours, 0.9 ml of concentrated sulfuric acid were added, heating under reflux was continued a further hour, the reaction solution was filtered and the filtrate was adjusted to a pH of 6.5 with 1N sodium hydroxide. After evaporation of the solution, the residue was heated in ethanol, again filtered and the filtrate was evaporated to a small volume. On cooling down, a crystalline 1:1 mixture of the title compound and the compound of Example 48, of m.p. 275°–276° C. was obtained.

EXAMPLE 52

2β,3aβ,6aα-Octahydrocyclpenta[b]pyrrole-2-carboxylic acid (a) 1,2,3,4,6,7-Hexahydro-5H-1-pyrind-2-one A mixture of 1 mole of cyclopentanone, 1 mole of acrylonitrile, 0.05 mole of ammonium acetate and 3 ml of 30% strength ammonia were heated in a pressure vessel for 3 hours at 220° C. The mixture was filtered through silica gel with ethyl acetate/cyclohexane (1:1) and the residue obtained after evaporation of the filtrate was recrystallized from cyclohexane. The product melted at 118° to 120° C.

$^1$H NMR data:
9.4 (broad s, 1H); 3.2–2.0 (m, 12H).

(b) Octahydro-trans-5H-1-pyrind-2-one

This compound was prepared in analogy to the procedure described in Example 51 under (b).

$^1$H NMR data: 7.8 (broad s, 1H); 2.9 (broad s, 1H); 2.6–2.2 (m, 2H); 2.1–1.0 (m, 8H).

(c) 3,3-Dichlorooctahydro-trans-5H-1-pyrind-2-one

This compound was prepared in analogy to the procedure described in Example 51 under (c).

$^1$H NMR data: 7.9 (broad s, 1H); 3.8 (broad s, 1H); 3.2–2.0 (m, 2H); 2.1–1.0 (m, 6H).

(d) 3-Chlorooctahydro-trans-5H-1-pyrind-2-one

This compound was prepared in analogy to the procedure described in Example 51 under (d).

¹H NMR data: 7.8 (broad s, 1H); 4.6–4.3 (m, 1H); 3.3–3.0 (m, 1H); 2.1 (d, J=6 Hz, 2H); 1.8–1.1 (m, 6H).

(e)
2β,3aβ,6aα-Octahydrocyclopenta[b]pyrrole-2-carboxylic acid

This compound was prepared in analogy to the procedure described in Example 51 under (e).
¹H NMR data: 4.7–4.4 (m, 1H); 3.0–0.9 (m, 10H).

EXAMPLE 53

2β,3aβ,8aα-Decahydrocyclohepta[b]pyrrole-2-carboxylic acid (a) 1,2,3,4,5,6,7,8-Octahydrocyclohepta[b]pyrid-2-one This compound was prepared in analogy to the procedure described in Example 51 under (a), starting from cycloheptanone.
¹H NMR data: 9.4 (broad s, 1H); 3.2–2.0 (m, 14H).

(b) Trans-Decahydrocyclohepta[b]pyrid-2-one

This compound was prepared in analogy to the procedure described in Example 51 under (b), starting from the compound previously mentioned under (a).
¹H NMR data: 7.9 (broad s, 1H); 2.9 (broad s, 1H); 2.6–2.2 (m, 2H); 2.1–1.0 (m, 12H).

(c)
3,3-Dichloro-trans-decahydrocyclohepta[b]pyrid-2-one

This compound was prepared in analogy to the procedure described in Example 51 under (c).
¹H NMR data: 7.9 (broad s, 1H); 3.8 (broad s, 1H); 3.2–2.0 (m, 2H); 2.1–1.0 (m, 10H).

(d) 3-Chloro-trans-decahydrocyclohepta[b]pyrid-2-one

This compound was prepared in analogy to the procedure described in Example 51 under (d).
¹H NMR data: 7.8 (broad s, 1H); 4.6–4.3 (m, 1H); 3.3–3.0 (m, 1H); 2.1 (d, J=6 Hz, 2H); 1.8–1.1 (m, 10H).

(e)
2β,3aβ,8aα-Decahydrocyclohepta[b]pyrrole-2-carboxylic acid

This compound was prepared in analogy to the procedure described in Example 51 under (e).
¹H NMR data: 4.7–4.4 (m, 1H); 3.2–1.1 (m, 1H).

EXAMPLE 54

Tert.-butyl 2β,3aα,7aβ-octahydroindole-2-carboxylate hydrochloride

This compound was prepared from 2β,3aα,7aβ-octahydroindole-2-carboxylic acid in analogy to the procedure described in Example 8.
¹H NMR data: 4.7–4.4 (m, 1H); 3.2–1.1 (m, 12H); 1.2 (s, 9H).

The compounds in the following Examples 55 to 59 were prepared in analogy to the procedure described in Example 8.

EXAMPLE 55

Tert.-butyl 2β,3aβ,7aα-octahydroindole-2-carboxylate hydrochloride

¹H NMR data: 4.7–4.3 (m, 1H); 3.4–1.1 (m, 12H); 1.2 (s, 9H).

EXAMPLE 56

Tert.-butyl 2β,3aα,6aβ-octahydrocyclopenta[b]pyrrole-2-carboxylate hydrochloride ¹H NMR data: 4.8–4.4 (m, 1H); 3.4–1.2 (m, 10H); 1.2 (s, 9H).

EXAMPLE 57

Tert.-butyl 2β,3aβ,6aα-octahydrocyclopenta[b]pyrrole-2-carboxylate hydrochloride ¹H NMR data: 4.8–4.4 (m, 1H); 3.5–1.2 (m, 10H); 1.2 (s, 9H).

EXAMPLE 58

Tert.-butyl 2β,3aα,8aβ-decahydrocyclohepta[b]pyrrole-2-carboxylate hydrochloride ¹H NMR data: 4.7–4.4 (m, 1H); 3.3–1.0 (m, 14H); 1.2 (s, 9H).

EXAMPLE 59

Tert.-butyl 2β,3aβ,8aα-decahydrocyclohepta[b]pyrrole-2-carboxylate hydrochloride ¹H NMR data: 4.7–4.3 (m, 1H); 3.2–0.8 (m, 14H); 1.2 (s, 9H).

EXAMPLE 60

Tert.-butyl N-(S-alanyl)-2S,3aR,7aS-octahydroindole-2-carboxylate hydrochloride (a) Tert.-butyl N-(N'-benzyloxycarbonyl-S-alanyl)-2S,3aR,7aS-octahydroindole-2-carboxylate This compound was prepared from Z-alanine in analogy to the procedure described in Example 36 under (a), and separated from its isomer as described there.
¹H NMR data: 7.4 (s, 5H); 5.3–4.8 (m, 1H); 4.2–3.7 (m, 2H); 3.1–1.4 (m, 11H); 1.3 (d, J=7 Hz, 3H); 1.2 (s, 9H).

(b) The compound mentioned above under (a) was hydrogenated with palladium/barium sulfate in 1N ethanolic hydrogen chloride, the desired title compound being obtained.
¹H NMR data: 5.2–4.8 (m, 1H); 4.2–3.7 (m, 2H); 3.1–1.4 (m, 11H); 1.3 (d, J=7 Hz, 3H); 1.2 (s, 9H).

The compounds in the following Examples 61 to 65 were prepared in analogy to the procedures described in Example 60 under (a) and (b).

EXAMPLE 61

Tert.-butyl N-(S-alanyl)-2S,3aS,7aR-octahydroindole-2-carboxylate hydrochloride

¹H NMR data: 5.2–4.7 (m, 1H); 4.4–3.8 (m, 2H); 3.1–1.4 (m, 11H); 1.25 (d, J=7 Hz, 3H); 1.2 (s, 9H).

EXAMPLE 62

Tert.-butyl N-(S-alanyl)-2S,3aR,6aS-octahydrocyclopenta-[b]pyrrole-2-carboxylate hydrochloride ¹H NMR data: 5.3–4.7 (m, 1H); 4.4–3.8 (m, 2H); 3.1–1.4 (m, 9H); 1.3 (d, J=7 Hz, 3H); 1.2 (s, 9H).

EXAMPLE 63

Tert.-butyl N-(S-alanyl)-2S,3aS,6aR-octahydrocyclopenta-[b]pyrrole-2-carboxylate hydrochloride $^1$H NMR data: 5.3–4.7 (m, 1H); 4.4–3.8 (m, 2H); 3.1–1.4 (m, 9H); 1.3 (d, J=7 Hz, 3H); 1.2 (s, 9H).

EXAMPLE 64

Tert.-butyl N-(S-alanyl)-2S,3aR,8aS-decahydrocyclohepta-[b]pyrrole-2-carboxylate hydrochloride $^1$H NMR spectrum: 5.1–4.6 (m, 1H); 4.5–3.7 (m, 2H); 3.1–1.4 (m, 13H); 1.3 (d, J=7 Hz, 3H); 1.2 (s, 9H).

EXAMPLE 65

Tert.-butyl N-(S-alanyl)-2S,3aS,8aR-decahydrocyclohepta-[b]pyrrole-2-carboxylate hydrochloride $^1$H NMR data: 5.1–4.6 (m, 1H); 4.5–3.7 (m, 2H); 3.1–1.4 (m, 13H); 1.3 (d, J=7 Hz, 3H); 1.2 (s, 9H).

EXAMPLE 66

N-(1S-Carboethoxy-3-phenylpropyl)-S-alanyl-2S,3aR,7aS-octahydroindole-2-carboxylic acid This compound was prepared in analogy to the procedure described in Example 39 under (a), starting from tert.-butyl N-(S-alanyl)-2S,3aR,7aS-octahydroindole-2-carboxylate. The tert.-butyl group was split off with trifluoroacetic acid.

EXAMPLE 67

N-(1S-Carboethoxy-3-keto-3-phenylpropyl)-S-alanyl-2S,3aR,7aS-octahydroindole-2-carboxylic acid This compound was prepared in analogy to the procedure described in Example 40, starting from tert.-butyl N-(S-alanyl)-2S,3aR,7aS-octahydroindole-2-carboxylate. The tert.-butyl group was split off with trifluoroacetic acid.

$^1$H NMR data: 1.2 (d+t, 6H); 1.3–3.6 (m, 16H); 4.2 (q, 2H); 4.1–4.6 (m, 4H); 7.3–8.1 (m, 5H).

EXAMPLE 68

N-(1S-Carboethoxy-3-keto-3-phenylpropyl)-S-alanyl-2S,3aS,7aR-octahydroindole-2-carboxylic acid This compound was prepared in analogy to the procedure described in Example 40, starting from tert.-butyl N-(S-alanyl)-2S,3aS,7aR-octahydroindole-2-carboxylate. The tert.-butyl group was split off with trifluoroacetic acid.

$^1$H NMR data: 1.2 (d+t, 6H); 1.3–3.6 (m, 16H); 4.2 (q, 2H); 4.1–4.6 (m, 4H); 7.3–8.1 (m, 5H).

EXAMPLE 69

N-(1S-Carboethoxy-3-keto-3-phenylpropyl)-S-alanyl-2S,3aR,6aS-octahydrocyclopenta[b]pyrrole-2-carboxylic acid This compound was prepared in analogy to the procedure described in Example 40, starting from tert.-butyl N-(S-alanyl)-2S,3aR,6aS-octahydrocyclopenta[b]pyrrole-2-carboxylate. The tert.-butyl group was split off with trifluoroacetic acid.

$^1$H NMR data: 1.1 (d, 3H); 1.35 (t, 3H); 1.0–3.7 (m, 14H); 4.2 (q, 2H); 4.0–4.7 (m, 4H); 7.3–8.0 (m, 5H).

EXAMPLE 70

N-(1S-Carboethoxy-3-keto-3-phenylpropyl)-S-alanyl-2S,3aS,6aR-octahydrocyclopenta[b]pyrrole-2-carboxylic acid This compound was prepared in analogy to the procedure described in Example 41, followed by splitting off the tert.-butyl group with trifluoroacetic acid.

$^1$H NMR data: 1.1 (d, 3H); 1.35 (t, 3H); 1.0–3.8 (m, 14H); 4.2 (q, 2H); 4.0–4.7 (m, 4H); 7.2–8.1 (m, 5H).

EXAMPLE 71

N-(1S-Carboethoxy-3-keto-3-phenylpropyl)-S-alanyl-2S,3aR,8aS-decahydrocyclohepta[b]pyrrole-2-carboxylic acid This compound was prepared in analogy to the reaction procedure described in Example 41, following by splitting off the tertiary butyl group with trifluoroacetic acid.

$^1$H NMR data: 1.2 (d, 3H); 1.4 (t, 3H); 1.2–3.8 (m, 18H); 4.1 (q, 2H); 4.0–4.6 (m, 4H); 7.2–8.2 (m, 5H).

EXAMPLE 72

N-(1S-Carboethoxy-3-keto-3-phenylpropyl)-S-alanyl-2S,3aS,8aR-decahydrocyclohepta[b]pyrrole-2-carboxylic acid This compound was prepared in analogy to the procedure described in Example 41, followed by cleaving off the tert.-butyl group with trifluoroacetic acid.

$^1$H NMR data: 1.2 (d+t, 6H); 1.2–3.8 (m, 18H); 4.2 (q, 2H); 4.0–4.6 (m, 4H); 7.1–8.1 (m, 5H).

EXAMPLE 73

N-(1S-Carboethoxy-3-hydroxy-3-phenylpropyl)-S-alanyl-2S,3aR,7aS-octahydroindole-2-carboxylic acid This compound was prepared in analogy to the procedure described in Example 33.

$^1$H NMR data: 1.2 (d, 3H); 1.3 (t, 3H); 1.3–3.8 (m, 16H); 4.2 (q, 2H); 4.0–4.6 (m, 4H); 4.7 (d, 1H); 7.1–7.4 (m, 5H).

EXAMPLE 74

N-(1S-Carboethoxy-3-hydroxy-3-phenylpropyl)-S-alanyl-2S,3aS,6aR-octahydrocyclopenta[b]pyrrole-2-carboxylic acid This compound was prepared in analogy to the procedure described in Example 33.

$^1$H NMR data: 1.2 (d+t, 3H); 1.1–3.9 (m, 14H); 4.2 (q, 2H); 4.0–4.7 (m, 4H); 4.8 (d, 1H); 7.1–7.4 (m, 5H).

EXAMPLES 75 TO 80

The compounds mentioned in these examples were prepared in analogy to the procedure described in Example 20.

EXAMPLE 75

N-(1S-Carboxy-3-phenylpropyl)-S-alanyl-2S,3aR,7aS-octahydroindole-2-carboxylic acid $^1$H NMR data: 1.2 (d, 3H); 1.2–3.8 (m, 18H); 4.0–4.6 (m, 4H); 7.2 (s, 5H).

EXAMPLE 76

N-(1S-Carboxy-3-phenylpropyl)-S-alanyl-2S,3aS,7aR-octahydroindole-2-carboxylic acid $^1$H NMR spectrum: 1.2 (d, 3H); 1.2–3.8 (m, 18H); 4.0–4.6 (m, 4H); 7.2 (s, 5H).

EXAMPLE 77

N-(1S-Carboxy-3-phenylpropyl)-S-alanyl-2S,3aR,6aS-octahydrocyclopenta[b]pyrrole-2-carboxylic acid $^1$H NMR data: 1.2 (d, 3H); 1.1–3.7 (m, 16H); 4.0–4.6 (m, 4H); 7.2 (s, 5H).

EXAMPLE 78

N-(1S-Carboxy-3-phenylpropyl)-S-alanyl-2S,3aS,6aR-octahydrocyclopenta[b]pyrrole-2-carboxylic acid $^1$H NMR spectrum: 1.2 (d, 3H); 1.1–3.8 (m, 16H); 4.0–4.6 (m, 4H); 7.2 (s, 5H).

EXAMPLE 79

N-(1S-Carboxy-3-phenylpropyl)-S-alanyl-2S,3aR,6aS-decahydrocyclohepta[b]pyrrole-2-carboxylic acid $^1$H NMR data: 1.2 (d, 3H); 0.9–3.6 (m, 20H); 4.0–4.6 (m, 4H); 7.2 (s, 5H).

EXAMPLE 80

N-(1S-Carboxy-3-phenylpropyl)-S-alanyl-2S,3aS,8aR-decahydrocyclohepta[b]pyrrole-2-carboxylic acid $^1$H NMR data: 1.2 (d, 3H); 0.8–3.6 (m, 20H); 4.0–4.6 (m, 4H); 7.2 (s, 5H).

EXAMPLE 81

N-(1S-Carboxy-3-keto-3-phenylpropyl)-S-alanyl-2S,3aR,7aS-octahydroindole-2-carboxylic acid $^1$H NMR data: 1.2 (d, 3H); 0.9–3.6 (m, 16H); 3.9–4.7 (m, 4H); 7.1–8.2 (m, 5H).

EXAMPLE 82

N-(1S-Carboxy-3-keto-3-phenylpropyl)-S-alanyl-2S,3aS,7aR-octahydroindole-2-carboxylic acid $^1$H NMR data: 1.2 (d, 3H); 0.9–3.6 (m, 16H); 3.9–4.7 (m, 4H); 7.2–8.1 (m, 5H).

EXAMPLE 83

N-(1S-Carboxy-3-keto-3-phenylpropyl)-S-alanyl-2S,3aR-6aS-octahydrocyclopenta[b]pyrrole-2-carboxylic acid $^1$H NMR data: 1.2 (d, 3H); 1.1–3.7 (m, 14H); 3.9–4.6 (m, 4H); 7.2–8.1 (m, 5H).

EXAMPLE 84

N-(1S-Carboxy-3-keto-3-phenylpropyl)-S-alanyl-2S,3aS,6aR-octahydrocyclopenta[b]pyrrole-2-carboxylic acid $^1$H NMR data: 1.2 (d, 3H); 1.1–3.7 (m, 14H); 3.9–4.6 (m, 4H); 7.2–8.1 (m, 5H).

EXAMPLE 85

N-(1S-Carboxy-3-keto-3-phenylpropyl)-S-alanyl-2S,3aR,8aS-decahydrocyclohepta[b]pyrrole-2-carboxylic acid $^1$H NMR data: 1.2 (d, 3H); 1.1–3.7 (m, 18H); 3.9–4.6 (m, 4H); 7.3–8.2 (m, 5H).

EXAMPLE 86

N-(1S-Carboxy-3-keto-3-phenyl)-alanyl-2S,3aS,8aR-decahydrocyclohepta[b]pyrrole-2-carboxylic acid $^1$H NMR data: 1.2 (d, 3H); 1.1–3.7 (m, 18H); 3.9–4.6 (m, 4H); 7.3–8.2 (m, 5H).

EXAMPLE 87

N-(1S-Carboxy-3-hydroxy-3-phenylpropyl)-S-alanyl-2S,3aR,7aS-octahydroindole-2-carboxylic acid $^1$H NMR spectrum: 1.2 (d, 3H); 1.1–3.7 (m, 16H); 3.8–4.6 (m, 4H); 4.7 (m, 1H); 7.1–7.4 (m, 5H).

EXAMPLE 88

N-(1S-Carboxy-3-hydroxy-3-phenylpropyl)-S-alanyl-2S,3aS,6aR-octahydrocyclopenta[b]pyrrole-2-carboxylic acid $^1$H NMR data: 1.2 (d, 3H); 1.1–3.7 (m, 14H); 3.9–4.5 (m, 4H); 4.7 (d, 1H); 7.1–7.4 (m, 5H).

EXAMPLE 89

2β, 3aβ, 7aα-octahydroindole-2-carboxylic acid 290 g of the acetylamino derivative obtained in accordance with Example 1 were heated with 2N hydrochloric acid as indicated in Example 2. The mixture was evaporated in vacuo, the residue was taken up in 1 l of isopropanol and reduced with about 35 g of NaBH$_4$ which was added in portions in the course of 30 minutes. The reaction temperature was kept at 40°–50° C. The reaction was allowed to continue for about 4 hours, then the mixture was evaporated in vacuo, the pH was adjusted to 6.5 with dilute hydrochloric acid, solid sodium chloride was used to saturate, and the aminoacids were extracted several times with n-butanol. The residue remaining after concentration of the organic phase was fractionally crystallized from chloroform/diisopropyl ether as described in Example 2.

Yields: 40–60 g of 2β, 3α, 7aα-product; 20 g of a mixed fraction; 100–130 g 2β, 3aβ, 7aα-product.

In the same manner, 2β, 3aβ, 7aα-2-azabicyclo[5.3.0]-decane-3-carboxylic acid and 2β, 3aβ, 7aα-2-azabicyclo[6.3.0]-undecane-3-carboxylic acid can be prepared.

EXAMPLE 90

N-(1-S-Carbethoxy-3-phenyl-propyl)-O-ethyl-S-tyrosyl-2S,3aR,7aS-octahydroindole-2-carboxylic acid (a)

N-(1-R,S-Carbethoxy-3-phenyl-propyl)-O-ethyl-S-tyrosylbenzylester 24 g of benzoylacrylic acid ethyl ester are reacted in 100 ml of ethanol with 30 g of O-ethyl-S-tyrosinebenzyl ester in the presence of 0.5 ml of triethylamine, and after concentration of the solution and digestion of the residue with diethyl ether/petroleum ether (1:1) as well as drying in vacuo, 42 g of the compound indicated in the heading.

(b)

N-(1-R,S-Carbethoxy-3-phenyl-propyl)-O-ethyl-S-tyrosine 40 g of the compound obtained according to Example 90 a are hydrogenated in 800 ml of glacial acetic acid and 4 g of Pd/C (10%) at 100 bar and room temperature. After chromatography on silica gel with ethyl acetate/cyclohexane (1:3) as eluent and drying of the evaporation residue, 25 g of compound of the heading, m.p. 205°–213° C., nearly completely homogeneous according to thin-layer chromatography.

$C_{23}H_{29}NO_5$ (399,5) calc. C 69.15; H 7.31; N 3.50; found: C 69.5; H 7.4; N 3.3.

(c)
N-(1-S-Carbethoxy-3-phenyl-propyl)-O-ethyl-S-tyrosyl-2S,3aR,7aS-octahydroindole-2-carboxylic acid According to the operation mode described in Example 42b, 1.5 g of the benzyl ester described in Example 42 a are reacted with 2.5 g of N-(1-R,S-carbethoxy-3-phenyl-propyl)-O-ethyl-S-tyrosine, 1.3 g of dicyclohexylcarbodiimide and 0.8 g of 1-hydroxybenzotriazole. Chromatography of the crude product on silica gel with cyclohexane/ethyl acetate (1:1) as eluent gives 1 g of the compound of the heading in the form of a colorless oil. The $^1$H-NMR data and the mass spectrum correspond to the indicated structure.

The benzyl ester is hydrogenated according to the operation mode described in Example 42 a. 0.6 g of the compound of the heading is obtained as colorless, amorphous powder.

$^1$H-NMR-data: 7.3 (s, 5H); 7.1–6.5 (2d, 4H); 4.4–4.0 (m, 4H); 3.9–3.0 (m, 4H); 2.9–1.2 (m, 17H); 1.4 (t, 3H); 1,25 (t, 3H).

EXAMPLE 91

N-(1-S-carbethoxy-3-phenyl-propyl)-O-methyl-S-tyrosyl-2S,3aR,7aS-octahydroindole-2-carboxylic acid This compound is obtained according to the operation mode described in Example 90 with the use of O-methyl-tyrosine-benzyl ester instead of O-ethyl-tyrosine benzyl ester in the step analogous to 90 (a).

$^1$H-NMR-data: 7.2 (s, 5H); 7.1–6.5 (2d, 4H); 4.4–4.0 (m, 3H); 3.9–3.0 (m, 3H); 3.5 (s, 3H); 2.9–1.2 (m, 17H); 1.3 (t, 3H).

EXAMPLE 92

N-(1-S-carbethoxy-3-phenyl-propyl)-O-ethyl-S-tyrosyl-2S,3aS,7aR-octahydroindole-2-carboxylic acid Prepared according to the operation mode of Example 90 from the amino acid described in Example 51. The $^1$H-NMR data correspond to the indicated structure.

EXAMPLE 93

N-(1-S-carbethoxy-3-phenyl-propyl)-O-methyl-S-tyrosyl-2S,3aS,7aR-octahydroindole-2-carboxylic acid Prepared according to the operation mode described in Example 91 with the use of the amino acid described in Example 51. The $^1$H-NMR data correspond to the indicated structure.

EXAMPLE 94

N-(1-S-carbethoxy-3-phenyl-propyl)-O-ethyl-S-tyrosyl-2S,3aR,6aS-octahydrocyclopenta[b]pyrrole-2-carboxylic acid Prepared according to the operation mode of Example 90 with the use of the amino acid described in Example 52.

$^1$H-NMR-data: 7.3 (s, 5H); 7.2–6.6 (2d, 4H); 4.4–3.9 (m, 4H); 3.9–3.0 (m, 4H); 2.9–1.2 (m, 15H); 1.35 (t, 3H); 1.25 (t, 3H).

EXAMPLE 95

N-(1-S-carbethoxy-3-phenyl-propyl)-O-methyl-S-tyrosyl-2S,3aR,6aS-octahydrocyclopenta[b]pyrrole-2-carboxylic acid Prepared according to the operation mode of Example 91 with the use of the amino acid described in Example 52. The $^1$H-NMR-data correspond to the indicated structure.

EXAMPLE 96

N-(1-S-carbethoxy-3-phenyl-propyl)-O-ethyl-S-tyrosyl-2S,3aS,6aR-octahydrocyclopenta[b]pyrrole-2-carboxylic acid Prepared according to the operation mode described in Example 90. The analysis data correspond to the indicated structure.

EXAMPLE 97

N-(1-S-carbethoxy-3-phenyl-propyl)-O-methyl-S-tyrosyl-2S,3aS,6aR-octahydrocyclopenta[b]pyrrole-2-carboxylic acid Prepared according to the operation mode described in Example 91. The analysis data correspond to the indicated structure.

We claim:

1. A compound of the formula

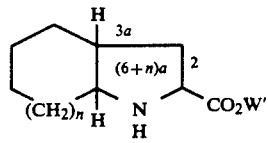

wherein the H atoms on the C atoms in the 3a- and (6+n)a-positions are in the trans configuration relative to one another n is 0, 1 or 2; and W' is hydrogen or a group which can be cleaved by hydrogenolysis or acid hydrolysis.

2. A compound as in claim 1 wherein W' is hydrogen, alkyl having 1 to 18 C atoms, or aralkyl having 7 to 10 C atoms.

3. A compound as in claim 1 wherein the hydrogen atoms on the bridgehead C atom in the 3a-position and on the C atom in the 2-position of the bicyclic ring system are on the same side of the reference plane of the ring atoms.

4. A compound as in claim 1 wherein the hydrogen atoms on the bridgehead C atom in the 3a-position and on the C atom in the 2-position of the bicyclic ring system are on the opposite side of the reference plane of the ring atoms.

5. 2β,2aα,7aβ-Octahydroindole-2-carboxylic acid.

* * * * *

UNITED STATES PATENT AND TRADEMARK OFFICE
CERTIFICATE OF CORRECTION

PATENT NO. : 5,008,400

DATED : April 16, 1991

INVENTOR(S) : Urbach et al.

It is certified that error appears in the above-identified patent and that said Letters Patent is hereby corrected as shown below:

COLUMN 36:
Claim 5, line 1, change "2a$\alpha$" to --3a$\alpha$--.

Signed and Sealed this

Ninth Day of June, 1992

Attest:

DOUGLAS B. COMER

*Attesting Officer*     *Acting Commissioner of Patents and Trademarks*